US008802628B2

(12) United States Patent
Fretzen et al.

(10) Patent No.: US 8,802,628 B2
(45) Date of Patent: Aug. 12, 2014

(54) STABLE SOLID FORMULATION OF A GC-C RECEPTOR AGONIST POLYPEPTIDE SUITABLE FOR ORAL ADMINISTRATION

(75) Inventors: Angelika Fretzen, Somerville, MA (US); Steven Witowski, Melrose, MA (US); Alfredo Grossi, Somerville, MA (US); Hong Zhao, Lexington, MA (US); Mahendra Dedhiya, Pomona, NY (US); Yun Mo, Commack, NY (US)

(73) Assignees: Ironwood Pharmaceuticals, Inc., Cambridge, MA (US); Forest Laboratories Holdings, Ltd., Hamilton (BM)

( * ) Notice: Subject to any disclaimer, the term of this patent is extended or adjusted under 35 U.S.C. 154(b) by 709 days.

(21) Appl. No.: 12/541,410

(22) Filed: Aug. 14, 2009

(65) Prior Publication Data

US 2010/0048489 A1    Feb. 25, 2010

Related U.S. Application Data

(60) Provisional application No. 61/089,422, filed on Aug. 15, 2008, provisional application No. 61/273,332, filed on Aug. 3, 2009, provisional application No. 61/231,725, filed on Aug. 6, 2009.

(51) Int. Cl.
  *A61K 38/10* (2006.01)
  *A61P 1/00* (2006.01)

(52) U.S. Cl.
  CPC ..................................... *A61K 38/10* (2013.01)
  USPC .......................................................... 514/14

(58) Field of Classification Search
  None
  See application file for complete search history.

(56) References Cited

U.S. PATENT DOCUMENTS

| | | | |
|---|---|---|---|
| 4,544,568 A | | 10/1985 | Heyland et al. |
| 4,992,419 A | * | 2/1991 | Woog et al. ..................... 514/7.7 |
| 5,221,495 A | | 6/1993 | Cao |
| 5,451,410 A | | 9/1995 | Milstein et al. |
| 5,593,696 A | * | 1/1997 | McNally et al. ............... 424/472 |
| 5,654,278 A | * | 8/1997 | Sørensen ..................... 514/11.3 |
| 5,904,935 A | | 5/1999 | Eckenhoff et al. |
| 6,068,850 A | | 5/2000 | Stevenson et al. |
| 6,124,261 A | | 9/2000 | Stevenson et al. |
| 6,541,606 B2 | | 4/2003 | Margolin et al. |
| 6,734,162 B2 | | 5/2004 | Van Antwerp et al. |
| 6,828,303 B2 | | 12/2004 | Kim et al. |
| 6,979,437 B2 | | 12/2005 | Bartus et al. |
| 6,995,200 B2 | | 2/2006 | Krohnke |
| 7,056,942 B2 | | 6/2006 | Hildesheim et al. |
| 7,141,254 B2 | | 11/2006 | Bhaskaran et al. |
| 7,304,036 B2 | | 12/2007 | Currie et al. |
| 7,351,798 B2 | | 4/2008 | Margolin et al. |
| 7,371,727 B2 | | 5/2008 | Currie et al. |
| 7,494,979 B2 | | 2/2009 | Currie et al. |
| 7,704,947 B2 | | 4/2010 | Currie et al. |
| 7,745,409 B2 | | 6/2010 | Currie et al. |
| 7,767,644 B2 | | 8/2010 | Schumann et al. |
| 7,772,188 B2 | | 8/2010 | Currie et al. |
| 7,910,546 B2 | | 3/2011 | Currie et al. |
| 8,080,526 B2 | | 12/2011 | Currie et al. |
| 8,101,579 B2 | | 1/2012 | Currie et al. |
| 8,110,553 B2 | | 2/2012 | Currie et al. |
| 2003/0003563 A1 | | 1/2003 | Vinkemeier et al. |
| 2003/0069182 A1 | | 4/2003 | Rinella |
| 2003/0073628 A1 | | 4/2003 | Shailubhai et al. |
| 2003/0104996 A1 | | 6/2003 | Li et al. |
| 2003/0175230 A1 | | 9/2003 | Dubief |
| 2004/0265242 A1 | | 12/2004 | Bartus et al. |
| 2004/0266989 A1 | * | 12/2004 | Currie et al. .................. 530/326 |
| 2005/0020811 A1 | * | 1/2005 | Currie et al. .................. 530/327 |
| 2007/0122354 A1 | | 5/2007 | Hastedt et al. |
| 2007/0154406 A1 | | 7/2007 | Moon et al. |
| 2007/0202165 A1 | * | 8/2007 | Heuer et al. ................... 424/464 |
| 2009/0110729 A1 | | 4/2009 | Giovannone et al. |
| 2009/0253634 A1 | | 10/2009 | Currie et al. |
| 2009/0305993 A1 | | 12/2009 | Currie |
| 2010/0221329 A1 | * | 9/2010 | Shailubhai et al. ........... 424/463 |
| 2012/0009225 A1 | | 1/2012 | Fretzen et al. |
| 2012/0039949 A1 | | 2/2012 | Fretzen et al. |
| 2012/0213846 A1 | | 8/2012 | Fretzen et al. |
| 2013/0190239 A1 | | 7/2013 | Fretzen et al. |

FOREIGN PATENT DOCUMENTS

| | | |
|---|---|---|
| JP | 64-009938 | 1/1989 |
| JP | 2003-201256 | 7/2003 |
| WO | WO9012029 | 10/1990 |
| WO | WO9104743 | 4/1991 |

(Continued)

OTHER PUBLICATIONS

Andresen et al ("Effect of 5 Days Linaclotide on Transit and Bowel Function in Females With Constipation-Predominant Irritable Bowel Syndrome" (Sep. 2007) 133(3): 761-768).*
Ahmed, Hashim and Shah, Navnit., "Formulations of Low Dose Medicines—Theory and Practice." American Pharmaceutical Review, 3(3): 1-4, 2000.
Andresen et al., "Effect of 5 Days Linaclotide on Transit and Bowel Function in Females With Constipation—Predominant Irritable Bowel Syndrome." Gastroenterology, 133 (3): 761-768, 2007.
Andresen et al., "Linaclotide Acetate." Drugs of the Future, 33(7): 570-576, 2008.
Camilleri et al., "Challenges to the Therapeutic Pipeline for Irritable Bowel Syndrome: End Points and Regulatory Hurdles." Gastroenterology, 135(6): 1877-1891, 2008.

(Continued)

*Primary Examiner* — Jean Witz
*Assistant Examiner* — Mindy Newman
(74) *Attorney, Agent, or Firm* — Honigman Miller Schwartz and Cohn; Kelly T. Murphy; Jonathan P. O'Brien

(57) ABSTRACT

Solid, stable formulations of linaclotide suitable for oral administration are described herein as are methods for preparing such formulations. The formulations described herein contain a polypeptide consisting of the amino acid sequence Cys Cys Glu Tyr Cys Cys Asn Pro Ala Cys Thr Gly Cys Tyr ("linaclotide"; SEQ ID NO:1) or a pharmaceutically acceptable salt thereof. The linaclotide formulations described herein are stable and have a sufficient shelf life for manufacturing, storing and distributing the drug.

26 Claims, 1 Drawing Sheet

(56) References Cited

FOREIGN PATENT DOCUMENTS

| | | |
|---|---|---|
| WO | WO9703692 | 2/1997 |
| WO | WO9704796 | 2/1997 |
| WO | WO9800152 | 1/1998 |
| WO | WO9800157 | 1/1998 |
| WO | WO0004880 | 2/2000 |
| WO | WO 00/32172 | 6/2000 |
| WO | WO0226248 | 4/2002 |
| WO | WO02062369 | 8/2002 |
| WO | WO02078683 | 10/2002 |
| WO | WO03014304 | 2/2003 |
| WO | WO 2004/052343 | 6/2004 |
| WO | WO 2005/014025 | 2/2005 |
| WO | WO 2005/042029 | 5/2005 |
| WO | WO2005087797 | 9/2005 |
| WO | WO 2007/044375 | 4/2007 |
| WO | WO2008006125 | 1/2008 |
| WO | WO2008021133 | 2/2008 |
| WO | WO2008027854 | 3/2008 |
| WO | WO2008106429 | 9/2008 |
| WO | WO2008151257 | 12/2008 |
| WO | WO 2010/065751 | 6/2010 |
| WO | WO 2011/019819 | 2/2011 |

OTHER PUBLICATIONS

Capasso et al., "Deamidation via Cyclic Imide of Asparaginyl Peptides: Dependence on Salts, Buffers and Organic Solvents." Peptide Research, 4(4): 234-238, 1991.

Cleland et al., "The Development of Stable Protein Formulations: A Close Look at Protein Aggregation, Deamidation, and Oxidation." Critical Reviews in Therapeutic Drug Carrier Systems, 10(4): 307-377, 1993.

Fu et al., "Protein Stability in Controlled-Release Systems." Nature Biotechnology, 18: 24-25, 2000.

Kirby, "Oil-Based Formulations for Oral Delivery of Therapeutic Peptides." Journal of Liposome Research, 10(4): 391-407, 2000.

Microbia, Forest, "Microbia and Forest Laboratories Announce Preliminary Results of Linaclotide Phase 2B Studies." Communications of Microbia, pp. 1-4, 2008.

Oliyai et al., "Chemical Pathways of Peptide Degradation. VII. Solid State Chemical Instability of an Aspartyl Residue in a Model Hexapeptide." Pharmaceutical Research, 11(6): 901-908, 1994.

Oliyai et al., "Solid State Chemical Instability of an Asparaginyl Residue in a Model Hexapeptide." Journal of Pharmaceutical Science & Technology, 48(3): 167-173, 1994.

"International Nonproprietary Names for Pharmaceutical Substances (INN)." WHO Drug Information, 21(3): 247-264, 2007.

Aventis Pharmaceuticals, Inc. (2002). DDAVP (desmopressin acetate) tablet, [Product Label]. Bridgewater, NJ 08807, USA.

Bedu-Addo, F. et al., "Preformulation Development of Recombinant Pegylated Staphylokinase SY161 Using Statistical Design." AAPS PharmSci (http://www.aapspharmsci.org), 4(4) article 19, 1-11, 2002.

Bedu-Addo, F.K. et al., "Use of Biophysical Characterization in Preformulation Development of a Heavy-Chain Fragment of Botulinum Serotype B: Evaluation of Suitable Purification Process Conditions." Pharmaceutical Research, 21(8):1353-1361, 2004.

Carpenter et al., "Rational Design of Stable Lyophilized Protein Formulations: Some Practical Advice." Pharmaceutical Research, 14(8): 969-975, 1997.

Chourasia, M.K. and Jain, S.K., "Pharmaceutical approaches to colon targeted drug delivery systems." J Pharm Pharmaceut Sci (www. ualberta.ca/-csps), 6(1):33-66, 2003.

Elan Pharmaceuticals, Inc. (2004). PRIALT (zinconitide) injection, solution, [Product Label]. San Diego, CA 92121, USA.

Fix, J.A., "Oral Controlled Release Technology for Peptides: Status and Future Prospects." Pharmaceutical Research, 13(12): 1760-1764, 1996.

Mehta, N.M., "Oral Delivery and Recombinant Production of Peptide Hormones. Part I: Making Oral Delivery Possible: Enteric-coated capsules or tablets with additional excipients enable intestinal delivery." Bio-Pharm International (www.biopharm-mag.com), 1-6, Jun. 2004.

Mehta, N.M., "Oral Delivery and Recombinant Production of Peptide Hormones. Part II: Recombinant Production of Therapeutic Peptides." Bio-Pharm International (www.biopharrn-mag.com), 7-9, Jun. 2004.

Patel, K. and Borchardt, R.T., "Chemical Pathways of Peptide Degradation. III. Effect of Primary Sequence on the Pathways of Deamidation of Asparaginyl Residues in Hexapeptides." Pharmaceutical Research, 7(8): 787-793, 1990.

Patel, K. and Borchardt, R.T., "Deamidation of Asparaginyl Residues in Proteins: A Potential Pathway for Chemical Degradation of Proteins in Lyophilized Dosage Forms." Journal of Parenteral Science & Technology, 44 (6):300-301, 1990.

Sejourne, F. et al., "Development of a Novel Bioactive Formulation of Vasoactive Intestinal Peptide in Sterically Stabilized Liposomes." Pharmaceutical Research, 14(3):362-365, 1997.

Constantino, H.R, et al., "Moisture-Induced Aggregation of Lyophilized Insulin". Pharmaceutical Research, 11(1): 21-29, 1994.

Cook et al., "Chronic constipation: Overview and Challenges." Neurogastroenterology and Motility, 21(supp2): 1-8, 2009.

Dulbecco et al., "Plaque formation and isolation of pure liner with poliomyelitis viruses." Journal of Experimental Medicine, 99(2): 167-182, 1954.

Grenha et al., "Chitosan nanoparticles are compatible with respiratory epithelial cells in vitro." European Journal of Pharmaceutical Sciences, 31: 73-84, 2007.

Lechuga-Ballesteros et al., "Trileucine Improves Aerosol Performance and Stability of Spray-dried Powders for Inhalation." Journal of Pharmaceutical Sciences, 97(1): 287-302, 2008.

Reporter's Guide to Irritable Bowel Syndrome, retrieved from <<http:www.aboutibs.org/pdfs/ReportersGuideIBS.pdf>> on Nov. 28, 2012, total of 18 pages where the main text is numbered as pp. 1-14.

Shailubhai et al., "Uroguanylin treatment suppresses polyp formation in the Apc(Min/+) mouse and induces apoptosis in human colon adenocarcinoma cells via cyclic GMP." Cancer Res., 60:5151-5157, 2000.

Vippagunta et al., "Crystalline solids." Advanced Drug Delivery Reviews, 48:3-26, 2001.

Langer, R. "Drug delivery and targeting", Nature; 392 (Supp): 5-10, 1998.

* cited by examiner

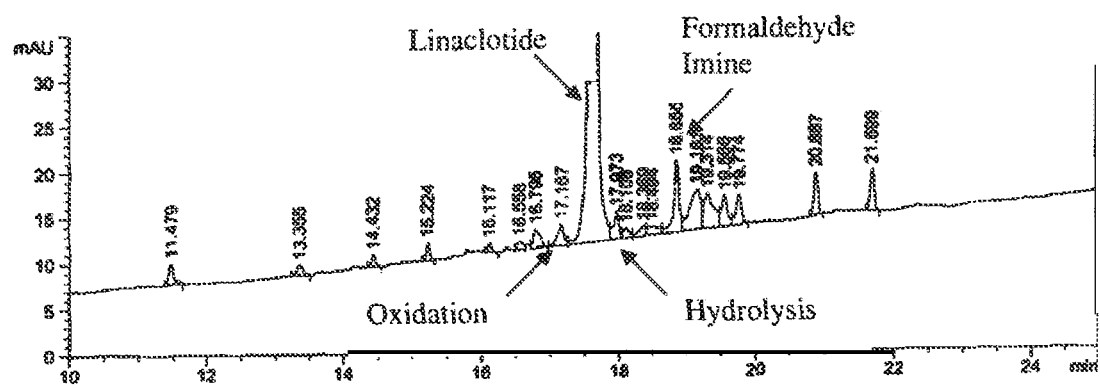

_US 8,802,628 B2_

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 1

Cys Cys Glu Tyr Cys Cys Asn Pro Ala Cys Thr Gly Cys Tyr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 2

Cys Cys Glu Tyr Cys Cys Asp Pro Ala Cys Thr Gly Cys Tyr
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: Formaldehyde bonded to Cys1
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 3

Cys Cys Glu Tyr Cys Cys Asn Pro Ala Cys Thr Gly Cys Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<223> OTHER INFORMATION: Cys1 is oxidized.
<220> FEATURE:
<221> NAME/KEY: DISULFID
<222> LOCATION: (2)..(10)
<220> FEATURE:
<221> NAME/KEY: DISULFID
```

```
<222> LOCATION: (5)..(13)

<400> SEQUENCE: 4

Cys Cys Glu Tyr Cys Cys Asn Pro Ala Cys Thr Gly Cys Tyr
1               5                   10
```

STABLE SOLID FORMULATION OF A GC-C RECEPTOR AGONIST POLYPEPTIDE SUITABLE FOR ORAL ADMINISTRATION

PRIORITY CLAIM

This application claims priority to U.S. Application Ser. No. 61/089,422, filed Aug. 15, 2008 and to the U.S. Application Ser. No. 61/273,332 filed Aug. 3, 2009 and to the U.S. Application Ser. No. 61/231,725 filed Aug. 6, 2009. The entire contents of the aforementioned applications are incorporated herein by reference.

FIELD

This disclosure concerns solid formulations of a guanylate cyclase-C receptor agonist polypeptide suitable for oral administration and methods for preparing such formulations.

SEQUENCE LISTING

This application incorporates by reference in its entirety the Sequence Listing entitled "IW057US1_ST25.txt" (1.2 kilobytes), which was created Mar. 13, 2013 and filed electronically herewith.

BACKGROUND

Many therapeutic polypeptides are formulated in aqueous solution because they are most active in this form. However, most polypeptides are not particularly stable in aqueous solution, such that the formulations often have a short half-life and require refrigeration. Although aqueous solutions of polypeptides can be dried by freeze-drying, spray-drying or other methods, such dried formulations may also be unstable and have reduced activity relative to an aqueous solution of the polypeptide. Typical break-down mechanisms that occur both in aqueous solution and in dried formulations include aggregation and oxidative or hydrolytic degradation. Thus, the majority of therapeutic polypeptides, whether in aqueous solution or dried, are stored under refrigerated conditions due to their limited stability.

Linaclotide is a peptide having the amino acid sequence Cys Cys Glu Tyr Cys Cys Asn Pro Ala Cys Thr Gly Cys Tyr (SEQ ID NO: 1) that activates the guanylate cyclase-C (GC-C) receptor. Linaclotide, which may be administered orally, is useful for the treatment of gastrointestinal disorders and conditions, including irritable bowel syndrome (IBS) and chronic constipation (CC). Formulations comprising linaclotide have needed to be refrigerated in order to avoid degradation over time. However, refrigeration is inconvenient both for commercial distribution of the drug and for storage by patients. Thus, there is a need to have a solid linaclotide formulation that is stable at room temperature for at least 12 months.

SUMMARY

Solid, stable formulations of linaclotide suitable for oral administration are described herein as are methods for preparing such formulations. The formulations described herein contain a polypeptide consisting of the amino acid sequence Cys Cys Glu Tyr Cys Cys Asn Pro Ala Cys Thr Gly Cys Tyr ("linaclotide", SEQ ID NO:1) or a pharmaceutically acceptable salt thereof.

The linaclotide formulations described herein are stable and have a sufficient shelf life for manufacturing, storing and distributing the drug. For example, formulations described herein are expected to have a shelf life of at least 12 months at room temperature storage conditions (e.g., 25° C./60% relative humidity (RH)). In further embodiments, the formulations described herein are expected to have a shelf life of at least 18 months or at least 24 months at room temperature storage conditions (e.g., 25° C./60% RH).

In some embodiments, formulations are described wherein ≥95% of the original amount of linaclotide in the composition remains after three months when packaged samples are stored at accelerated conditions (40° C./75% RH) when assessed in an assay on a weight/weight basis as determined by high pressure liquid chromatography (HPLC) against a linaclotide reference standard. In further embodiments, ≥90% of the original amount of linaclotide in the composition remains after at least 6 months when packaged samples are stored at accelerated conditions (40° C./75% RH). In other embodiments, formulations are described wherein chromatographic purity of the linaclotide as determined as area percent by HPLC remains at ≥95% over the course of at least three months when packaged samples are stored at accelerated conditions (40° C./75% RH). In further embodiments, the chromatographic purity of the linaclotide as determined by area percent by HPLC remains at ≥90% over the course of at least 6 months when packaged samples are stored at accelerated conditions (40° C./75% RH). Thus, for example, no more than about 10% of the linaclotide undergoes degradation to other products such as an oxidation product of linaclotide, a hydrolysis product of linaclotide or a formaldehyde-mediated imine product of linaclotide ("formaldehyde imine product").

In one embodiment, the invention comprises a pharmaceutical composition comprising linaclotide, wherein the chromatographic purity of the linaclotide decreases by less than 10% after 18 months or 24 months of storage of the pharmaceutical composition at 25° C. at 60% relative humidity in a sealed container containing a desiccant. In a further embodiment, the chromatographic purity of the linaclotide decreases by less than 9%, 8%, 7%, 6%, 5%, 4% or 2% after 18 months or 24 months of storage of the pharmaceutical composition at 25° C. at 60% relative humidity in a sealed container containing a desiccant. In another embodiment, the invention comprises a pharmaceutical composition comprising linaclotide, wherein the chromatographic purity of the linaclotide decreases by less than 10% after 3 months or 6 months of storage of the pharmaceutical composition at 40° C. at 75% relative humidity in a sealed container containing a desiccant. In a further embodiment, the chromatographic purity of the linaclotide decreases by less than 9%, 8%, 7%, 6%, 5%, 4% or 2% after 3 months or 6 months of storage of the pharmaceutical composition at 40° C. at 75% relative humidity in a sealed container containing a desiccant.

In one embodiment, the invention comprises a unit dosage form of a pharmaceutical composition comprising linaclotide, wherein the chromatographic purity of the linaclotide decreases by less than 10% after 18 months or 24 months of storage of the unit dosage form at 25° C. at 60% relative humidity in a sealed container containing a desiccant. In a further embodiment, the chromatographic purity of the linaclotide decreases by less than 9%, 8%, 7%, 6%, 5%, 4% or 2% after 18 months or 24 months of storage of the unit dosage form at 25° C. at 60% relative humidity in a sealed container containing a desiccant. In another embodiment, the invention comprises a unit dosage form of a pharmaceutical composition comprising linaclotide, wherein the chromatographic purity of the linaclotide decreases by less than 10% after 3 months or 6 months of storage of the unit dosage form at 40° C. at 75% relative humidity in a sealed container containing a desiccant. In a further embodiment, the chromatographic purity of the linaclotide decreases by less than 9%, 8%, 7%, 6%, 5%, 4% or 2% after 3 months or 6 months of storage of the unit dosage form at 40° C. at 75% relative humidity in a sealed container containing a desiccant.

In one embodiment, the invention comprises a sealed container comprising a plurality of unit dosage forms of a pharmaceutical composition comprising linaclotide, wherein the chromatographic purity of the linaclotide decreases by less than 10% after 18 months or 24 months of storage of the sealed container containing a desiccant at 25° C. at 60% relative humidity. In a further embodiment, the chromatographic purity of the linaclotide decreases by less than 9%, 8%, 7%, 6%, 5%, 4% or 2% after 18 months or 24 months of storage of the sealed container containing a desiccant at 25° C. at 60% relative humidity. In another embodiment, the invention comprises a sealed container comprising a plurality of unit dosage forms of a pharmaceutical composition comprising linaclotide, wherein the chromatographic purity of the linaclotide decreases by less than 10% after 3 months or 6 months of storage of the sealed container containing a desiccant at 40° C. at 75% relative humidity. In a further embodiment, the chromatographic purity of the linaclotide decreases by less than 9%, 8%, 7%, 6%, 5%, 4% or 2% after 3 months or 6 months of storage of the sealed container containing a desiccant at 40° C. at 75% relative humidity.

In one embodiment, the invention comprises a pharmaceutical composition comprising linaclotide, wherein the assay value for linaclotide determined on a weight/weight basis decreases by less than 10% after 18 months or 24 months of storage of the pharmaceutical composition at 25° C. at 60% relative humidity in a sealed container containing a desiccant. In a further embodiment, the assay value for linaclotide determined on a weight/weight basis decreases by less than 9%, 8%, 7%, 6%, 5%, 4%, 3%, 2% or 1% after 18 months or 24 months of storage of the pharmaceutical composition at 25° C. at 60% relative humidity in a sealed container containing a desiccant. In another embodiment, the invention comprises a pharmaceutical composition comprising linaclotide, wherein the assay value for linaclotide determined on a weight/weight basis decreases by less than 10% after 3 months or 6 months of storage of the pharmaceutical composition at 40° C. at 75% relative humidity in a sealed container containing a desiccant. In a further embodiment, the chromatographic purity of the linaclotide decreases by less than 9%, 8%, 7%, 6%, 5%, 4%, 3%, 2% or 1% after 3 months or 6 months of storage of the pharmaceutical composition at 40° C. at 75% relative humidity in a sealed container containing a desiccant.

In one embodiment, the invention comprises a unit dosage form of a pharmaceutical composition comprising linaclotide, wherein the assay value for linaclotide determined on a weight/weight basis decreases by less than 10% after 18 months or 24 months of storage of the unit dosage form at 25° C. at 60% relative humidity in a sealed container containing a desiccant. In a further embodiment, the assay value for linaclotide determined on a weight/weight basis decreases by less than 9%, 8%, 7%, 6%, 5%, 4%, 3%, 2% or 1% after 18 months or 24 months of storage of the unit dosage form at 25° C. at 60% relative humidity in a sealed container containing a desiccant. In another embodiment, the invention comprises a unit dosage form of a pharmaceutical composition comprising linaclotide, wherein the assay value for linaclotide determined on a weight/weight basis decreases by less than 10% after 3 months or 6 months of storage of the unit dosage form at 40° C. at 75% relative humidity in a sealed container containing a desiccant. In a further embodiment, the assay value for linaclotide determined on a weight/weight basis decreases by less than 9%, 8%, 7%, 6%, 5%, 4%, 3%, 2% or 1% after 3 months or 6 months of storage of the unit dosage form at 40° C. at 75% relative humidity in a sealed container containing a desiccant.

In one embodiment, the invention comprises a sealed container comprising a plurality of unit dosage forms of a pharmaceutical composition comprising linaclotide, wherein the assay value for linaclotide determined on a weight/weight basis decreases by less than 10% after 18 months or 24 months of storage of the sealed container at 25° C. at 60% relative humidity in a sealed container containing a desiccant. In a further embodiment, the assay value for linaclotide determined on a weight/weight basis decreases by less than 9%, 8%, 7%, 6%, 5%, 4%, 3%, 2% or 1% after 18 months or 24 months of storage of the sealed container containing a desiccant at 25° C. at 60% relative humidity. In another embodiment, the invention comprises a sealed container comprising a plurality of unit dosage forms of a pharmaceutical composition comprising linaclotide, wherein the assay value for linaclotide determined on a weight/weight basis decreases by less than 10% after 3 months or 6 months of storage of the sealed container containing a desiccant at 40° C. at 75% relative humidity. In a further embodiment, the assay value for linaclotide determined on a weight/weight basis decreases by less than 9%, 8%, 7%, 6%, 5%, 4%, 3%, 2% or 1% after 3 months or 6 months of storage of the sealed container containing a desiccant at 40° C. at 75% relative humidity.

In some embodiments, there is provided a pharmaceutical composition comprising linaclotide and a hydrolysis product comprising:

(SEQ ID NO: 2)

H-Cys-Cys-Glu-Tyr-Cys-Cys-Asp-Pro-Ala-Cys-Thr-Gly-Cys-Tyr-OH

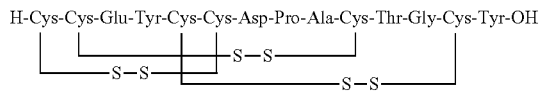

In some embodiments, the hydrolysis product comprises less than about 15% by weight of the composition, less than about 10% by weight of the composition, less than about 7% by weight of the composition or less than about 5% by weight of the composition. In other embodiments, the hydrolysis product comprises from about 0.01% to about 15% by weight of the composition, about 0.05% to about 10% by weight of the composition, about 0.05% to about 7% by weight of the composition or about 0.05% to about 5% by weight of the composition. In further embodiments, there is provided a method of treating a gastrointestinal disorder in a patient in need thereof comprising administering a pharmaceutical composition comprising linaclotide and a hydrolysis product.

In some embodiments, there is provided a pharmaceutical composition comprising linaclotide and a formaldehyde imine product comprising:

(SEQ ID NO: 3)

H₂C═Cys-Cys-Glu-Tyr-Cys-Cys-Asn-Pro-Ala-Cys-Thr-Gly-Cys-Tyr-OH

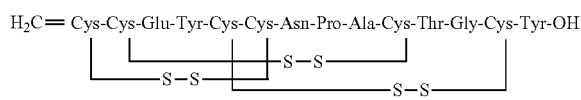

In some embodiments, the formaldehyde imine product comprises less than about 15% by weight of the composition, less than about 10% by weight of the composition, less than about 7% by weight of the composition or less than about 5% by weight of the composition. In other exemplary embodiments, the formaldehyde imine product comprises from about 0.01% to about 15% by weight of the composition, about 0.05% to about 10% by weight of the composition, about 0.05% to about 7% by weight of the composition or about 0.05% to about 5% by weight of the composition. In further embodiments, there is provided a method of treating a gastrointestinal disorder in a patient in need thereof comprising administering a pharmaceutical composition comprising linaclotide and a formaldehyde imine product.

In some embodiments, there is provided a pharmaceutical composition comprising linaclotide and a linaclotide oxidation product. In one embodiment, the linaclotide oxidation product has a molecular weight of 1542.8, which most likely forms as the addition of a single oxygen atom to one of the six cysteinyl sulfurs in linaclotide. One potential structure of the product is depicted below, although one of skill in the art will recognize that the oxygen atom may be attached to any of the other five sulfurs:

(SEQ ID NO: 4)

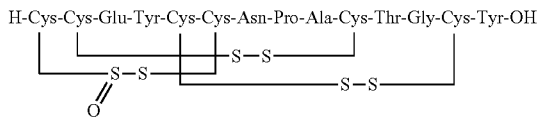

In another embodiment, there may be an addition of more than one oxygen atom to linaclotide, which would increase its molecular weight by 16 AU per added oxygen atom.

In some embodiments, the linaclotide oxidation product comprises less than about 15% by weight of the composition, less than about 10% by weight of the composition, less than about 7% by weight of the composition or less than about 5% by weight of the composition. In other exemplary embodiments, the linaclotide oxidation product comprises from about 0.01% to about 15% by weight of the composition, about 0.05% to about 10% by weight of the composition, about 0.05% to about 7% by weight of the composition or about 0.05% to about 5% by weight of the composition. In further embodiments, there is provided a method of treating a gastrointestinal disorder in a patient in need thereof comprising administering a pharmaceutical composition comprising linaclotide and a linaclotide oxidation product.

The assay value on a weight/weight basis ("weight/weight assay") may be determined by comparing, e.g., by HPLC, the amount of linaclotide in a sample, to a linaclotide reference standard. As used herein, the weight of linaclotide in a composition after storage at room temperature or accelerated conditions at a specified time point (e.g., three or six months of storage under accelerated conditions [40° C./75% RH] or 12, 18 or 24 months of storage under room temperature conditions [25° C./60% RH]) is compared to the weight of linaclotide in a composition at an initial time (e.g., the time when the pharmaceutical composition is released for clinical or patient use ("the release date")) to provide the weight/weight assay value. For example, the weight of linaclotide in a composition is measured after storage for a specified time at accelerated conditions (40° C./75% RH) and compared to the weight of linaclotide that was present in the sample at the release date. In another example, the weight of linaclotide in a composition is measured after storage for a specified time at room temperature conditions (25° C./60% RH) and compared to the weight of linaclotide that was present in the sample at the release date. Thus, the phrase "≧90% of the original amount of linaclotide in the composition remains after at least 6 months when packaged samples are stored at accelerated conditions (40° C./75% RH)" means the weight of linaclotide in the composition measured in an assay on a weight/weight basis as determined by HPLC after at least 6 months storage at accelerated conditions is ≧90% of the amount of linaclotide in the composition present at the initial time (e.g., the release date of the linaclotide composition).

Chromatographic purity of linaclotide may be assessed by performing HPLC under the conditions described herein. The area under the linaclotide peak is measured and compared to the total area under all peaks excluding the solvent peak and any non-polypeptide related peaks (i.e., peaks associated with excipients that may be observed in a placebo). As used herein, the chromatographic purity of linaclotide in a composition after storage at room temperature or accelerated conditions at a specified time point (e.g., three or six months of storage under accelerated conditions [40° C./75% RH] or 12, 18 or 24 months of storage under room temperature conditions [25° C./60% RH]) is compared to the chromatographic purity of linaclotide in a composition at an initial time (e.g., the time when the pharmaceutical composition is released for clinical or patient use ("the release date")) to provide the chromatographic purity value. For example, the chromatographic purity of linaclotide in a composition is measured after storage for a specified time at accelerated conditions (40° C./75% RH) and compared to the chromatographic purity of linaclotide in the composition at the release date. In another example, the chromatographic purity of linaclotide in a composition is measured after storage for a specified time at room temperature conditions (25° C./60% RH) and compared to the chromatographic purity of linaclotide in the composition at the release date.

This disclosure features a method for preparing a pharmaceutical composition comprising linaclotide or a pharmaceutically acceptable salt thereof, the method comprising: (a) providing a solution, e.g., an aqueous solution ("the coating solution"), comprising: (i) linaclotide or a pharmaceutically acceptable salt thereof; (ii) a cation selected from $Mg^{2+}$, $Ca^{2+}$, $Zn^{2+}$, $Mn^{2+}$, $K^+$, $Na^+$ or $Al^{3+}$ and/or a sterically hindered primary amine (e.g., leucine) and, optionally, (iii) a pharmaceutically acceptable binder; and (b) applying the coating solution to a pharmaceutically acceptable filler to generate polypeptide-coated filler (e.g., by spraying, mixing or coating the pharmaceutically acceptable filler with the coating solution). The method can optionally include one or more of: (i) blending the polypeptide-coated filler with a pharmaceutically acceptable glidant, a pharmaceutically acceptable lubricant or a pharmaceutically acceptable additive that acts as both a glidant and lubricant; (ii) blending the polypeptide-coated filler with filler that is not polypeptide-coated, (iii) blending the polypeptide-coated filler with other additives; (iii) applying a pharmaceutically acceptable coating additive to the polypeptide-coated filler. The final pharmaceutical composition can be placed into capsules (e.g., gelatin capsule) or used to form tablets.

It has been found that a cation selected from $Mg^{2+}$, $Ca^{2+}$, $Zn^{2+}$, $Mn^{2+}$, $K^+$, $Na^+$ or $Al^{3+}$ is useful for suppressing the formation of an oxidation product of linaclotide during storage. It has also been found that a sterically hindered primary amine, e.g., leucine, is useful for suppressing the formation of a formaldehyde imine adduct of linaclotide ("formaldehyde imine product") during storage. Thus, a linaclotide formulation comprising a cation selected from $Mg^{2+}$, $Ca^{2+}$, $Zn^{2+}$, $Mn^{2+}$, $K^+$, $Na^+$ or $Al^{3+}$ (e.g., a divalent cation selected from $Zn^{2+}$, $Mg^{2+}$ or $Ca^{2+}$) and/or a sterically hindered primary amine, such as an amino acid, has a sufficient shelf life (as measured by chromatographic purity and/or by a weight/ weight assay) for manufacturing, storing and distributing the drug. Further, while the presence of a sterically hindered amine alone can increase the formation of a hydrolysis product of linaclotide during storage, the combination of a sterically hindered primary amine and a cation, e.g., the combination of leucine and $Ca^{2+}$, suppresses the formation of the hydrolysis product of linaclotide as well as the oxidation product of linaclotide during storage, leading to an even greater overall stability as determined by a weight/weight assay and/or by chromatographic purity.

In some embodiments, there is provided a pharmaceutical composition comprising a pharmaceutically acceptable carrier, linaclotide and one or more agents selected from $Mg^{2+}$, $Ca^{2+}$, $Zn^{2+}$, $Mn^{2+}$, $K^+$, $Na^+$ or $Al^{3+}$ and a sterically hindered primary amine, wherein the agent improves at least one attribute of the composition, relative to a pharmaceutical composition without said agent. In further embodiments, the agent is $Mg^{2+}$, $Ca^{2+}$ or $Zn^{2+}$. In a further embodiment, the agent is $Ca^{2+}$. In some embodiments, the cation is provided as, without limitation, magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate. In further embodiments, the cation is provided as magnesium chloride, calcium chloride, calcium phosphate, calcium sulfate, zinc acetate, manganese chloride, potassium chloride, sodium chloride or aluminum chloride. In other embodiments, the cation is provided as calcium chloride, magnesium chloride or zinc acetate.

In another embodiment, the agent is a sterically hindered primary amine. In a further embodiment, the sterically hindered primary amine is an amino acid. In yet a further embodiment, the amino acid is a naturally-occurring amino acid. In a still further embodiment, the naturally-occurring amino acid is selected from the group consisting of: histidine, phenylalanine, alanine, glutamic acid, aspartic acid, glutamine, leucine, methionine, asparagine, tyrosine, threonine, isoleucine, tryptophan, methionine and valine; yet further, the naturally-occurring amino acid is leucine, isoleucine, alanine or methionine; in another embodiment, the naturally-occurring amino acid is leucine or methionine; still further, the naturally-occurring amino acid is leucine. In another embodiment, the sterically hindered primary amine is a non-naturally occurring amino acid or amino acid derivative (e.g., 1-aminocyclohexane carboxylic acid, lanthionine or theanine). In a further embodiment, the sterically hindered primary amine is cyclohexylamine, 2-methylbutylamine or chitosan.

In other embodiments, there is provided a pharmaceutical composition comprising a pharmaceutically acceptable carrier, linaclotide, a cation selected from $Mg^{2+}$, $Ca^{2+}$, $Zn^{2+}$, $Mn^{2+}$, $K^+$, $Na^+$ or $Al^{3+}$ (e.g., a divalent cation selected from $Zn^{2+}$, $Mg^{2+}$ or $Ca^{2+}$) and a sterically hindered primary amine. In one embodiment, the cation is $Ca^{2+}$. In another embodiment, the cation is a mixture of two or three of $Mg^{2+}$, $Ca^{2+}$, $Zn^{2+}$, $Mn^{2+}$, $K^+$, $Na^+$ or $Al^{3+}$ (e.g., a mixture of two or three of $Zn^{2+}$, $Mg^{2+}$ or $Ca^{2+}$). In a further embodiment, the pharmaceutical composition further comprises a pharmaceutically acceptable binder and/or a pharmaceutically acceptable glidant, lubricant or additive that acts as both a glidant and lubricant and/or an antioxidant. In a further embodiment, the sterically hindered primary amine is an amino acid. In yet a further embodiment, the amino acid is a naturally-occurring amino acid. In a still further embodiment, the naturally-occurring amino acid is selected from the group consisting of: histidine, phenylalanine, alanine, glutamic acid, aspartic acid, glutamine, leucine, methionine, asparagine, tyrosine, threonine, isoleucine, tryptophan, methionine and valine; yet further, the naturally-occurring amino acid is leucine, isoleucine, alanine or methionine; in another embodiment, the naturally-occurring amino acid is leucine or methionine; still further, the naturally-occurring amino acid is leucine. In another embodiment, the sterically hindered primary amine can be a mixture of more than one sterically hindered primary amines. For example, the sterically hindered primary amine may be a mixture of two or more sterically hindered primary amines, e.g., a mixture of two or more amino acids.

In some cases the molar ratio of cation:sterically hindered primary amine:linaclotide (e.g., $Ca^{2+}$:leucine:linaclotide) in the aqueous solution applied to the carrier is 5-100:5-50:1. It can be desirable for the molar ratio of cation:sterically hindered primary amine (e.g., $Ca^{2+}$:leucine) to be equal to or greater than 2:1 (e.g., between 5:1 and 2:1). Thus, in some cases the molar ratio of cation:sterically hindered primary amine:linaclotide (e.g., $Ca^{2+}$:leucine:linaclotide) applied to the carrier is 100:50:1, 100:30:1, 80:40:1, 80:30:1, 80:20:1, 60:30:1, 60:20:1, 50:30:1, 50:20:1, 40:20:1, 20:20:1, 10:10:1, 10:5:1 or 5:10:1. When binder, e.g., methylcellulose, is present in the linaclotide solution applied to the carrier it can be present at 0.5%-2.5% by weight (e.g., 0.7%-1.7% or 0.7%-1% or 1.5% or 0.7%).

The weight of linaclotide applied to a given weight of filler (e.g., microcrystalline cellulose) can vary from about 0.02:100 to about 2.67:100. Thus, about 0.05 mg to about 6.0 mg of linaclotide can be applied to 225 mg of filler. In a further embodiment, the weight of linaclotide applied to a given weight of filler is about 0.05 mg to about 2.0 mg of linaclotide (e.g., 0.1, 0.2, 0.3. 0.4, 0.5, 0.6, 0.7 mg peptide for 225 mg of filler).

In various embodiments: the sterically hindered primary amine is an amino acid (e.g., a naturally-occurring amino acid or a naturally-occurring amino acid selected from histidine, phenylalanine, alanine, glutamic acid, aspartic acid, glutamine, methionine, asparagine, tyrosine, threonine, leucine, isoleucine, tryptophan, or valine). In other cases the sterically hindered primary amine is a non-naturally occurring amino acid or amino acid derivative (e.g., lanthionine, theanine or 1-amino cyclohexane). In other cases, the sterically hindered primary amine is an amino sugar (e.g., chitosan or glucosamine).

In some cases, the sterically hindered primary amine has the formula:

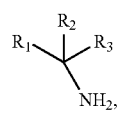

wherein $R_1$, $R_2$ and $R_3$ are independently selected from: H; —C(O)OH; C1-C6 alkyl, optionally substituted by —$CO_2H$, —$CONH_2$, or a 5-10 membered aryl or heteroaryl; C1-C6 alkoxyalkyl; or C1-C6 thioalkoxyalkyl, wherein any of the alkyl or aryl groups above can be singly or multiply substituted with halogen or —$NH_2$, and provided that no more than two of $R_1$, $R_2$ and $R_3$ are H. In a further embodiment, no more than one of $R_1$, $R_2$ and $R_3$ is H.

The term "alkyl", as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like.

The terms $C_{n-m}$ "alkoxyalkyl" and $C_{n-m}$ "thioalkoxyalkyl" mean alkyl, substituted with one or more alkoxy or thioalkoxy groups, as the case may be, wherein the combined total number of carbons of the alkyl and alkoxy groups, or alkyl and thioalkoxy groups, combined, as the case may be, is between the values of n and m. For example, a $C_{4-6}$ alkoxyalkyl has a total of 4-6 carbons divided between the alkyl and alkoxy portion; e.g. it can be —$CH_2OCH_2CH_2CH_3$, —$CH_2CH_2OCH_2CH_3$ or —$CH_2CH_2CH_2OCH_3$.

As used herein, the term "aryl" (as in "aryl ring" or "aryl group"), used alone or as part of a larger moiety, refers to a carbocyclic ring system wherein at least one ring in the system is aromatic and has a single point of attachment to the rest of the molecule. Unless otherwise specified, an aryl group may be monocyclic, bicyclic or tricyclic and contain 6-18 ring members. Examples of aryl rings include, but are not limited to, phenyl, naphthyl, indanyl, indenyl, tetralin, fluorenyl, and anthracenyl.

The term "heteroaryl" (or "heteroaromatic" or "heteroaryl group" or "aromatic heterocycle") used alone or as part of a larger moiety as in "heteroaralkyl" or "heteroarylalkoxy" refers to a ring system wherein at least one ring in the system is aromatic and contains one or more heteroatoms, wherein each ring in the system contains 3 to 7 ring members and which has a single point of attachment to the rest of the molecule. Unless otherwise specified, a heteroaryl ring system may be monocyclic, bicyclic or tricyclic and have a total of five to fourteen ring members. In one embodiment, all rings in a heteroaryl system are aromatic. Also included in this definition are heteroaryl radicals where the heteroaryl ring is fused with one or more aromatic or non-aromatic carbocyclic or heterocyclic rings, or combinations thereof, as long as the radical or point of attachment is in the heteroaryl ring. Bicyclic 6,5 heteroaromatic system, as used herein, for example, is a six membered heteroaromatic ring fused to a second five membered ring wherein the radical or point of attachment is on the six membered ring.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, benzopyrazinyl, benzopyranonyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In various cases: the antioxidant is selected from BHA (butylated hydroxyanisole), BHT (butylated hydroxytoluene), vitamin E, propyl gallate, ascorbic acid and salts or esters thereof, tocopherol and esters thereof, alpha-lipoic acid, beta-carotene; the pharmaceutically acceptable binder is polyvinyl alcohol or polyvinyl pyrrolidone; the pharmaceutically acceptable binder is selected from: a starch (e.g., corn starch, pre-gelatinized potato starch, rice starch, wheat starch, and sodium starch glycollate), maltodextrin or a cellulose ether (e.g., methylcellulose, ethylcellulose, carboxymethylcellulose, hydroxyethyl cellulose, hydroxyethyl methylcellulose, hydroxypropyl cellulose and hydroxypropyl methylcellulose); the pharmaceutically acceptable filler is cellulose (e.g., microfine cellulose or microcrystalline cellulose such as Celphere CP-305 or Avicel); the pharmaceutically acceptable filler is a sugar or a sugar alcohol (e.g., mannitol, isomalt, sorbitol, dextrose, xylitol, sucrose and lactose); the filler comprises particles having an average diameter between 50 μm and 1000 μm; the lubricant and/or glidant is selected from: talc, leucine, magnesium stearate, stearic acid and polyvinyl alcohol; and the lubricant and/or glidant is selected from: calcium stearate, mineral oil, vegetable oil, polyethylene glycol (PEG; e.g., PEG that is liquid or solid at room temperature), sodium benzoate, and sodium lauryl sulfate.

In some cases, the linaclotide solution used in a method for preparing the formulation has a pH below 7 (e.g., a pH between 1 and 3 or a pH between about 1.5 and about 2.5). The pH can be adjusted with, e.g., phosphoric acid. In some cases, the solution is buffered. Various pharmaceutically acceptable buffers can be used (e.g., phosphate buffer).

In some cases, the linaclotide solution used in a method for preparing the formulation comprises both a cation (e.g., $CaCl_2$) and a sterically hindered primary amine (e.g., leucine).

In some cases the linaclotide solution comprises $CaCl_2$ and leucine; the binder is methylcellulose; the filler is microcrystalline cellulose; the glidant and/or lubricant comprises talc or leucine.

Also provided is a pharmaceutical composition prepared by any of the methods described herein.

In another aspect, a pharmaceutical composition is disclosed that comprises a pharmaceutically acceptable carrier, linaclotide and one or more agents selected from (i) a cation selected from $Mg^{2+}$, $Ca^{2+}$, $Zn^{2+}$, $Mn^{2+}$, $K^+$, $Na^+$ or $Al^{3+}$, or (ii) a sterically hindered primary amine. In some embodiments, the pharmaceutical composition comprises at least one cation and at least one sterically hindered primary amine.

Methods of using the pharmaceutical compositions to treat a variety of gastrointestinal disorders are also described.

BRIEF DESCRIPTION OF THE FIGURE

FIG. 1 demonstrates an example of an analysis of linaclotide by HPLC, wherein "Oxidation" refers to the linaclotide oxidation product, "Formaldehyde Imine" refers to the linaclotide formaldehyde imine product and "Hydrolysis" refers to the linaclotide hydrolysis product.

This FIGURE is provided by way of example and is not intended to limit the scope of the present invention.

DETAILED DESCRIPTION

Oral compositions containing linaclotide can be used to treat a variety of gastrointestinal disorders. In various embodiments, the patient is suffering from a gastrointestinal disorder; the patient is suffering from a disorder selected from the group consisting of: gastrointestinal motility disorders, chronic intestinal pseudo-obstruction, colonic pseudo-obstruction, Crohn's disease, duodenogastric reflux, dyspepsia, functional dyspepsia, nonulcer dyspepsia, a functional gastrointestinal disorder, functional heartburn, gastroesophageal reflux disease (GERD), gastroparesis, irritable bowel syndrome, post-operative ileus, ulcerative colitis, chronic constipation, constipation, pain associated with constipation, and disorders and conditions associated with constipation (e.g. constipation associated with use of opiate pain killers, post-surgical constipation, and constipation associated with neuropathic disorders as well as other conditions and disorders described herein); the patient is suffering from a gastrointestinal motility disorder, chronic intestinal pseudo-obstruction, colonic pseudo-obstruction, Crohn's disease, duodenogastric reflux, dyspepsia, functional dyspepsia, nonulcer dyspepsia, a functional gastrointestinal disorder, functional heartburn, gastroesophageal reflux disease (GERD), gastroparesis, inflammatory bowel disease, irritable bowel syndrome (e.g. diarrhea-predominant irritable bowel syndrome (d-IBS), constipation-predominant irritable bowel syndrome (c-IBS) and/or alternating irritable bowel syndrome (a-IBS)), post-operative ileus, ulcerative colitis, chronic constipation, constipation, pain associated with constipation, and disorders and conditions associated with constipation (e.g. constipation associated with use of opiate pain killers, post-surgical constipation, and constipation associated with neuropathic disorders as well as other conditions and disorders described herein); the patient has been diagnosed with a functional gastrointestinal disorder according to the Rome Criteria (e.g. Rome II), the patient has been diagnosed with irritable bowel syndrome (e.g. (e.g. diarrhea predominant-IBS, constipation predominant-IBS, and/or alternating-IBS), according to the Rome Criteria (e.g. Rome II).

The dose range of linaclotide for adult humans is generally from 25 µg to 6 mg per day orally. In a further embodiment, the dose range is 25 µg to 2 mg per day orally. In some embodiments, the dose range for adult humans is 50 µg to 1 mg per day orally (e.g., 50 µg, 67.5 µg, 100 µg, 133 µg, 150 µg, 200 µg, 250 µg, 266 µg, 300 µg, 350 µg, 400 µg, 450 µg, 500 µg, 550 µg, 600 µg, 650 µg, 700 µg, 750 µg, 800 µg, 850 µg, 900 µg, 950 µg or 1 mg). In further embodiments, the dose range is 100 µg to 600 µg per day orally. In other embodiments, the dose is 50 µg, 67.5 µg, 100 µg, 133 µg, 150 µg, 200 µg, 266 µg, 300 µg, 400 µg, 500 µg or 600 µg linaclotide per day orally. In one embodiment, the linaclotide composition is provided in a discrete unit, a unit dosage form, (e.g., a tablet, a capsule, a sachet) that is effective at such dosage or as a multiple of the same. In certain embodiments, the unit dosage form and daily dose are equivalent. In various embodiments, the unit dosage form is administered with food at anytime of the day, without food at anytime of the day, with food after an overnight fast (e.g. with breakfast). In various embodiments, the unit dosage form is administered once a day, twice a day or three times a day. The unit dosage form can optionally comprise other additives. In some embodiments, one, two or three unit dosage forms will contain the daily oral dose of linaclotide. The precise amount of compound administered to a patient will be the responsibility of the attendant physician. However, the dose employed will depend on a number of factors, including the age and sex of the patient, the precise disorder being treated, and its severity.

In one embodiment, there is provided a method for treating irritable bowel syndrome with constipation (IBS-c) in an adult patient in need thereof, comprising administering to the patient once daily an effective amount of a pharmaceutical composition described herein. In various embodiments, the pharmaceutical composition comprises 133 µg or 266 µg linaclotide per unit dose per day. In other embodiments, the pharmaceutical composition is administered for a period of at least one day, two days, three days, four days, five days, six days, one week, two weeks, three weeks, four weeks or longer. In some embodiments, treatment with the linaclotide composition improves at least one symptom selected from reduced abdominal pain, an increase in the number of complete spontaneous bowel movements (CSBM) in a week, an increase in the number of spontaneous bowel movements (SBM) in a week, improved stool consistency, reduced straining, reduced abdominal discomfort, reduced bloating or reduced IBS-c symptom severity.

In one embodiment, there is provided a method for treating chronic constipation in an adult patient in need thereof, comprising administering to the patient once daily an effective amount of a pharmaceutical composition described herein. In various embodiments, the pharmaceutical composition comprises 133 µg or 266 µg linaclotide per unit dose per day. In other embodiments, the pharmaceutical composition is administered for a period of at least one day, two days, three days, four days, five days, six days, one week, two weeks, three weeks, four weeks or longer. In some embodiments, treatment with the linaclotide composition improves at least one symptom selected from an increase in the number of complete spontaneous bowel movements (CSBM) in a week, an increase in the number of spontaneous bowel movements (SBM) in a week, improved stool consistency, reduced straining, reduced abdominal discomfort, reduced bloating or reduced severity of constipation.

Stool consistency of each BM may be monitored by the 7-point Bristol Stool Form Scale (BSFS) (1=hard lumps, 2=lumpy sausage, 3=cracked sausage, 4=smooth sausage, 5=soft lumps, 6=mushy, 7=watery). Straining may be monitored by the 7-point Ease of Passage Scale (1=manual disimpaction/enema needed, 2=severe straining, 3=moderate straining, 4=mild straining, 5=no straining, 6=urgency, 7=incontinent). CSBM may be measured by the sensation of complete emptying after an SBM (yes/no). Abdominal discomfort, bloating and severity of constipation may be measured using, e.g., a 5-point ordinal scale (1=none, 2=mild, 3=moderate, 4=severe, 5=very severe).

A cation of the invention may be provided as a pharmaceutically acceptable salt i.e., a cation with an appropriate counterion. Examples of pharmaceutically acceptable salts that may be used in the invention include, without limitation, magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate. In some embodiments, the pharmaceutically acceptable salts include calcium chloride, calcium carbonate, calcium acetate, magnesium chloride, magnesium acetate, zinc acetate and zinc chloride. In further embodiments, a pharmaceutically acceptable salt that may be used is calcium chloride, magnesium chloride and zinc acetate.

As used herein, the term "binder" refers to any pharmaceutically acceptable binder that may be used in the practice of the invention. Examples of pharmaceutically acceptable binders include, without limitation, a starch (e.g., corn starch, potato starch and pre-gelatinized starch (e.g., STARCH 1500® and STARCH 1500 LM®, sold by Colorcon, Ltd.) and other starches), maltodextrin, gelatin, natural and synthetic gums such as acacia, powdered tragacanth, guar gum, cellulose and its derivatives (e.g., methylcellulose, hydroxyethyl cellulose, hydroxyethyl methylcellulose, hydroxypropyl cellulose and hydroxypropyl methylcellulose (hypromellose), ethyl cellulose, cellulose acetate, carboxymethyl cellulose calcium, sodium carboxymethyl cellulose, carboxymethylcellulose, microcrystalline cellulose (e.g. AVICEL™, such as, AVICEL-PH-101™, -103™ and -105™, sold by FMC Corporation, Marcus Hook, Pa., USA)), polyvinyl alcohol, polyvinyl pyrrolidone (e.g., polyvinyl pyrrolidone K30), and mixtures thereof.

As used herein, the term "filler" refers to any pharmaceutically acceptable filler that may be used in the practice of the invention. Examples of pharmaceutically acceptable fillers include, without limitation, talc, calcium carbonate (e.g., granules or powder), dibasic calcium phosphate, tribasic calcium phosphate, calcium sulfate (e.g., granules or powder), microcrystalline cellulose (e.g., Avicel PH101 or Celphere CP-305), powdered cellulose, dextrates, kaolin, mannitol, silicic acid, sorbitol, starch (e.g., Starch 1500), pre-gelatinized starch, lactose, glucose, fructose, galactose, trehalose, sucrose, maltose, isomalt, raffinose, maltitol, melezitose, stachyose, lactitol, palatinite, xylitol, myoinositol, and mixtures thereof.

Examples of pharmaceutically acceptable fillers that may be particularly used for coating with linaclotide include, without limitation, talc, microcrystalline cellulose (e.g., Avicel PH101 or Celphere CP-305), powdered cellulose, dextrates, kaolin, mannitol, silicic acid, sorbitol, starch, pre-gelatinized starch, lactose, glucose, fructose, galactose, trehalose, sucrose, maltose, isomalt, dibasic calcium phosphate, raffinose, maltitol, melezitose, stachyose, lactitol, palatinite, xylitol, mannitol, myoinositol, and mixtures thereof.

As used herein, the term "additives" refers to any pharmaceutically acceptable additive. Pharmaceutically acceptable additives include, without limitation, disintegrants, dispersing additives, lubricants, glidants, antioxidants, coating additives, diluents, surfactants, flavoring additives, humectants, absorption promoting additives, controlled release additives, anti-caking additives, anti-microbial agents (e.g., preservatives), colorants, desiccants, plasticizers and dyes.

As used herein, an "excipient" is any pharmaceutically acceptable additive, filler, binder or agent.

As used herein, "purified linaclotide" is linaclotide or a pharmaceutically acceptable salt thereof that is greater than or equal to 90 percent pure or greater than or equal to 95 percent pure. In some embodiments, linaclotide as used in the methods and compositions described herein is purified. Linaclotide purity can be measured, for example, by chromatographic purity of linaclotide using reversed phase HPLC as described in Example 21. Linaclotide Assay [w/w] can be determined, for example, by using reversed phase HPLC with quantitation via external calibration with a reference standard as described in Example 21.

In one aspect, the pharmaceutical composition may be prepared by spraying a solution comprising linaclotide or a pharmaceutically acceptable salt thereof, on a pharmaceutically acceptable filler to generate linaclotide-coated filler. In one embodiment, the method comprises: (a) providing a solution, e.g., an aqueous solution ("the coating solution"), comprising: (i) linaclotide or a pharmaceutically acceptable salt thereof; (ii) a cation selected from $Mg^{2+}$, $Ca^{2+}$, $Zn^+$, $Mn^{2+}$, $K^+$, $Na^+$ or $Al^{3+}$ and/or a sterically hindered primary amine (e.g., leucine) and, optionally, (iii) a pharmaceutically acceptable binder; and (b) applying the coating solution to a pharmaceutically acceptable filler to generate polypeptide-coated filler (e.g., by spraying, mixing or coating the pharmaceutically acceptable filler with the coating solution). The method can optionally include one or more of: (i) blending the polypeptide-coated filler with a pharmaceutically acceptable glidant, a pharmaceutically acceptable lubricant or a pharmaceutically acceptable additive that acts as both a glidant and lubricant; (ii) blending the polypeptide-coated filler with filler that is not polypeptide-coated, (iii) blending the polypeptide-coated filler with other additives; and (iv) applying a pharmaceutically acceptable coating additive to the polypeptide-coated filler. The final pharmaceutical composition can be placed into capsules (e.g., gelatin capsule) or used to form tablets.

In another embodiment, the pharmaceutical composition is prepared by spray drying, which is a technique used to prepare microparticles (e.g., microcapsules or microspheres) of drugs. Spray-dried peptides generally retain their biological activity upon dissolution and may have useful physical characteristics, including a uniform particle size and a spherical shape. In addition, the microparticles prepared by spray drying are often free flowing, which is helpful for pharmaceutical manufacturing processes such as forming tablets and filling capsules. Spray drying processes are also useful because they may be readily scaled up for clinical and commercial manufacturing.

Thus, this disclosure features a method for preparing a pharmaceutical composition comprising linaclotide or a pharmaceutically acceptable salt thereof, the method comprising: (a) providing a solution, e.g., an aqueous or organic solution, comprising: (i) linaclotide or a pharmaceutically acceptable salt thereof; and (ii) a cation selected from $Mg^{2+}$, $Ca^{2+}$, $Zn^{2+}$, $Mn^{2+}$, $K^+$, $Na^+$ or $Al^{3+}$ and/or a sterically hindered primary amine (e.g., leucine) and (b) spray drying the linaclotide-containing solution to produce microparticles. The linaclotide-containing solution can optionally include a polymer, such as one or more of the binders described herein, a lipid or phospholipid, and/or a filler, such as mannitol. The method can optionally include one or more additional steps of: (i) blending the linaclotide microparticles with a pharmaceutically acceptable glidant, a pharmaceutically acceptable lubricant or a pharmaceutically acceptable additive that acts as both a glidant and lubricant; (ii) blending the microparticles with a filler, and/or (iii) blending the microparticles with other additives. The final pharmaceutical composition can be placed into capsules (e.g., gelatin capsule) or used to form tablets.

In other embodiments, the pharmaceutical composition is prepared by spray freeze drying, supercritical fluid processing or lyophilization of a solution, e.g., an aqueous or organic solution, comprising: (i) linaclotide or a pharmaceutically acceptable salt thereof; and (ii) a cation selected from $Mg^{2+}$, $Ca^{2+}$, $Zn^{2+}$, $Mn^{2+}$, $K^+$, $Na^+$ or $Al^{3+}$ and/or a sterically hindered primary amine (e.g., leucine).

In some embodiments, the linaclotide composition is provided in a solid form for oral administration. Examples of such forms include, without limitation, a tablet, a sachet, a pellet, a capsule or a powder. In some embodiments, the compositions can be used to create unit dosages forms, e.g., tablets, capsules, sachets or pellets. Orally administered compositions can include, for example, binders, lubricants, inert diluents, lubricating, surface active or dispersing additives, flavoring additives, and humectants. Orally administered formulations such as tablets may optionally be coated or scored and may be formulated so as to provide sustained, delayed or controlled release of the linaclotide therein. The linaclotide can be co-administered or co-formulated with other medications. In one embodiment, the linaclotide composition can be co-administered with other medications used to treat gastrointestinal disorders. The linaclotide composition can also be used for treatment of disorders outside the gastrointestinal tract such as congestive heart failure and benign prostatic hypertrophy.

The compositions can include, for example, various additional solvents, dispersants, coatings, absorption promoting additives, controlled release additives, and one or more inert additives (which include, for example, starches, polyols, granulating additives, microcrystalline cellulose, diluents, lubricants, binders, disintegrating additives, and the like), etc. If desired, tablet dosages of the disclosed compositions may be coated by standard aqueous or non-aqueous techniques. Compositions can also include, for example, anti-caking additives, preservatives, sweetening additives, colorants, flavors, desiccants, plasticizers, dyes, and the like.

Suitable disintegrants include, for example, agar-agar, calcium carbonate, microcrystalline cellulose, croscarmellose sodium, crospovidone, povidone, polacrilin potassium, sodium starch glycolate, potato or tapioca starch, other starches, pre-gelatinized starch, clays, other algins, other celluloses, gums, and mixtures thereof.

Suitable lubricants include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Evonik Degussa Co., Plano, Tex. USA), a pyrogenic silicon dioxide (CAB-O-SIL, Cabot Co., Boston, Mass. USA), and mixtures thereof.

Suitable glidants include, for example, leucine, colloidal silicon dioxide, magnesium trisilicate, powdered cellulose, starch, talc, and tribasic calcium phosphate.

Suitable anti-caking additives include, for example, calcium silicate, magnesium silicate, silicon dioxide, colloidal silicon dioxide, talc, and mixtures thereof.

Suitable anti-microbial additives that may be used, e.g., as a preservative for the linaclotide compositions, include, for example, benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, and mixtures thereof.

Suitable coating additives include, for example, sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, and mixtures thereof. Suitable protective coatings include Aquacoat (e.g. Aquacoat Ethylcellulose Aqueous Dispersion, 15% w/w, FMC Biopolymer, ECD-30), Eudragit (e.g. Eudragit E PO PE-EL, Roehm Pharma Polymers) and Opadry (e.g Opadry AMB dispersion, 20% w/w, Colorcon).

In certain embodiments, suitable additives for the linaclotide composition include one or more of sucrose, talc, magnesium stearate, crospovidone or BHA.

In certain embodiments, the term "95%" may be 95.0%, the term "90%" may be 90.0%, the term "10%" may be 10.0%, the term "9%" may be 9.0%, the term "8%" may be 8.0%, the term "7%" may be 7.0%, the term "6%" may be 6.0%, the term "5%" may be 5.0%, the term "4%" may be 4.0%, the term "3%" may be 3.0%, the term "2%" may be 2.0%, and the term "1%" may be 1.0%.

In certain embodiments, the linaclotide composition is provided in a unit dosage form. In some embodiments, the unit dosage form is a capsule, a tablet, a sachet, a pellet or a powder. In one such embodiment, the unit dosage form is a capsule or tablet. Such unit dosage forms may be contained in a container such as, without limitation, a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to provide a single dosage form. For example, tablets or capsules may be contained in a bottle which is in turn contained within a box. In some embodiments, the unit dosage forms are provided in a container further comprising a desiccant. In a further embodiment, the unit dosage forms, e.g., a quantity of tablets or capsules, are provided in a container, e.g., a bottle, jar or re-sealable bag, containing a desiccant. In a further embodiment, the container containing the unit dosage forms is packaged with administration or dosage instructions. In certain embodiments, the linaclotide composition is provided in a kit. The linaclotide composition described herein and combination therapy agents can be packaged as a kit that includes single or multiple doses of two or more agents, each packaged or formulated individually, or single or multiple doses of two or more agents packaged or formulated in combination. Thus, the linaclotide composition can be present in first container, and the kit can optionally include one or more agents in a second container. The container or containers are placed within a package, and the package can optionally include administration or dosage instructions.

EXAMPLES

The following examples are merely illustrative of the present invention and should not be construed as limiting the scope of the invention in any way as many variations and equivalents that are encompassed by the present invention will become apparent to those skilled in the art upon reading the present disclosure.

Linaclotide or a pharmaceutically acceptable salt thereof may be produced and purified using standard techniques known in the art, e.g., chemical synthesis or recombinant expression followed by and purification using standard techniques.

Formulation Scheme A

Preparation of the Coating Solution:

Approximately 32 g to 42 g of purified water is mixed with hydrochloric acid to create a solution with a pH between 1.5 and 2.0. The cation, if used, is added to the solution in a quantity to provide the desired concentration, and the solution is mixed for sufficient time to produce a clear solution. The sterically hindered primary amine, if used, is added to the solution in a quantity to provide the desired concentration, and the solution is mixed for sufficient time to produce a clear solution. Other additives, such as antioxidants, are then added, if desired. The pH of the solution is tested, and hydrochloric acid is added, if necessary, to produce a solution having a pH between 1.5 and 2.0. The binder is then added to the solution and the mixture is then stirred for sufficient time to achieve a clear solution. The desired amount of linaclotide is added to the solution and mixed for 30-100 minutes to provide the coating solution.

Preparation of the Active Beads:

Approximately 30-36 g of dried microcrystalline cellulose beads are added to a Mini Column Fluid Bed Coater. The microcrystalline cellulose beads are fluidized and heated prior to layering. Next, the coating solution is layered to the beads. The spraying temperature is controlled between 24° C. and 55° C. by controlling inlet temperature, spray rate, atomization pressure, and air volume. After the entire coating solution is layered to the beads, the beads are dried. The product of this process is referred to as active beads.

Preparation of Active Beads with Protective Coating: Approximately 35 g of Active Beads are added to a Mini Column Fluid Bed Coater. The Active Beads are fluidized and heated prior to coating with Aquacoat (e.g. Aquacoat Ethylcellulose Aquaeous Dispersion, 15% w/w, FMC Biopolymer, ECD-30), Eudragit (e.g. Eudragit E PO PE-EL, Roehm Pharma Polymers) or Opadry (e.g Opadry AMB dispersion, 20% w/w, Colorcon). Next, the coating solution is layered to the beads. The spraying temperature is controlled between 24° C. and 55° C. by controlling inlet temperature, spray rate, atomization pressure, and air volume. After the entire coating solution is layered to the beads, the beads are dried.

Formulation Scheme B

Preparation of the Coating Solution:

Approximately 8.3 kg of purified water is mixed with hydrochloric acid to create a solution with a pH between 1.5 and 2.0. The cation, if used, is added to the solution in a quantity to provide the desired concentration, and the solution is mixed for sufficient time to produce a clear solution. The sterically hindered primary amine, if used, is added to the solution in a quantity to provide the desired concentration, and the solution is mixed for sufficient time to produce a clear solution. Other additives, such as antioxidants, are then added, if desired. The binder is then added to the solution and the solution is mixed for sufficient time to achieve a clear solution. The pH of the solution is tested, and hydrochloric acid is added if necessary to produce a solution having a pH between 1.5 and 2.0. This is Solution 1. Approximately 8.3 kg of purified water is mixed with hydrochloric acid to create a solution with a pH between 1.5 and 2.0. The desired amount of linaclotide is added to the solution and mixed for 10 to 30 minutes. The pH of the solution is tested, and hydrochloric acid is added if necessary to produce a solution having a pH between 1.5 and 2.0. This is Solution 2. Solution 1 and Solution 2 are then mixed together. The pH of the solution is tested, and hydrochloric acid is added if necessary to produce a solution having a pH between 1.5 and 2.0. This is the coating solution.

Preparation of the Active Beads:

Approximately 24.19 kg of microcrystalline cellulose beads are added to a Wurster Column of a Glatt GPCG-30 Fluid Bed. The microcrystalline cellulose beads are fluidized and heated to product temperature of 45-47° C. Next, the coating solution is layered to the beads. The product spraying temperature is controlled between 37° C. and 47° C. by controlling inlet temperature, spray rate, atomization pressure, and air volume. After the entire coating solution is layered to the beads, the beads are dried with a product drying temperature of 37° C. to 47° C. The product of this process is referred to as active beads.

Examples 1-15

Preparation of Linaclotide Formulations

The linaclotide formulations of Examples 1-15 were produced essentially as described in Formulation Scheme A wherein Table 1 provides the amounts of cation, sterically hindered primary amine, binder, linaclotide and beads, while Table 2 provides the conditions under which the beads were coated:

TABLE 1

| Example | Cation Amount [ ]* | Amine Amount [ ] | Binder Amount | Amount of Linaclotide** | Beads Amount |
|---|---|---|---|---|---|
| 1 | $CaCl_2 \cdot 2H_2O$ 0.6740 g [60] | Leucine 0.2005 g [20] | Hypromellose 1.019 g | 0.1282 g | Celphere CP-305 33.38 g |
| 2 | $CaCl_2 \cdot 2H_2O$ 0.6740 g [60] | Leucine 0.3007 g [30] | Hypromellose 0.3063 g | 0.1329 g | Celphere CP-305 33.87 g |
| 3 | $CaCl_2 \cdot 2H_2O$ 0.2247 g [20] | Leucine 1.002 g [100] | Hypromellose 0.0656 g | 0.1282 g | Celphere CP-305 33.86 g |
| 4 | $CaCl_2 \cdot 2H_2O$ 1.123 g [100] | Leucine 0.2005 g [20] | Hypromellose 1.969 g | 0.1282 g | Celphere CP-305 32.36 g |
| 5 | $CaCl_2 \cdot 2H_2O$ 0.4493 g [40] | Leucine 0.4009 g [40] | Hypromellose 0.5425 g | 0.1282 g | Celphere CP-305 33.78 g |
| 6 | $MgCl_2 \cdot 6H_2O$ 0.2590 g [10] | Leucine 0.3341 g [20] | Hypromellose 0.6636 g | 0.2100 g | Celphere CP-305 33.83 g |
| 7 | $ZnAc \cdot 2H_2O$ 0.2796 g [10] | Leucine 0.3341 g [20] | Hypromellose 0.6636 g | 0.2100 g | Celphere CP-305 33.82 g |
| 8 | N/A | Leucine 0.8944 g [27] | Hypromellose 0.6636 g | 0.4387 g | Celphere CP-305 33.40 g |
| 9 | $CaCl_2 \cdot 2H_2O$ 0.3745 g [10] | N/A | Hypromellose 0.6636 g | 0.4227 g | Celphere CP-305 33.83 g |
| 10 | N/A | N/A | Hypromellose 0.6811 g | 0.2114 g | Celphere CP-305 34.28 g |
| 11 | N/A | N/A | Hypromellose 0.6636 g | 0.4227 g | Celphere CP-305 34.13 g |

TABLE 1-continued

| Example | Cation Amount [ ]* | Amine Amount [ ] | Binder Amount | Amount of Linaclotide** | Beads Amount |
|---|---|---|---|---|---|
| 12 | CuCl$_2$•2H$_2$O 0.4342 g [10] | N/A | Hypromellose 0.6636 g | 0.4227 g | Celphere CP-305 33.79 g |
| 13 | ZnAc•2H$_2$O 0.5590 g [10] | N/A | Hypromellose 0.6636 g | 0.4227 g | Celphere CP-305 33.68 g |
| 14 | MgCl$_2$•6H$_2$O 0.5178 g [10] | N/A | Hypromellose 0.6636 g | 0.4227 g | Celphere CP-305 33.72 g |
| 15 | N/A | Methionine 0.0380 g [1] | Hypromellose 0.6636 g | 0.4387 g | Celphere CP-305 34.08 g |

*"Cation" refers to the divalent cation contained in the salt used in the example, "Amine" refers to the sterically hindered primary amine, [ ] refers to the molar ratio of the cation and/or amine to linaclotide.
**The Amount of linaclotide in this and all following examples is determined based on peptide content and chromatographic purity as listed on the Certificate of Analysis provided for each manufactured lot of linaclotide Active Pharmaceutical Ingredient (API).

TABLE 2

| Example | Product Spraying Temp (° C.) | Inlet Temp (° C.) | Spray rate (mL/min) | Atomization Pressure (psig) | Air Flow |
|---|---|---|---|---|---|
| 1 | 34.0-37.0 | 55.7-57.7 | 0.33-0.40 | 20 | Low |
| 2 | 27.4-32.3 | 37.01-42.1 | 0.40 | 22 | Low |
| 3 | 32.6-34.7 | 60.0-60.1 | 0.33-0.40 | 20 | Low |
| 4 | 35.3-39.3 | 58.9-59.2 | 0.40 | 18 | Low |
| 5 | 27.8-27.9 | 58.7-59.8 | 0.35-0.33 | 20 | Low |
| 6 | 32.1-38.3 | 42.0-53.4 | 0.39-0.75 | 22 | Low |
| 7 | 31.7-39.3 | 50.0-52.5 | 0.27-0.57 | 22 | Low |
| 8 | 33.3-41.3 | 50.5-57.0 | 0.57-0.65 | 22 | Low |
| 9 | 33.2-40.0 | 49.5-58.7 | 0.82-1.00 | 20 | Low |
| 10 | 42.5 | 59.5 | 0.49 | 22 | Low |
| 11 | 39.7 | 52.0 | 0.66 | 22 | Low |
| 12 | 36.6-40.0 | 47.2-54.8 | 0.65-0.75 | 20-22 | Low |
| 13 | 32.4 | 57.4 | 0.65 | 22 | Low |
| 14 | 34.0 | 49.0 | 0.75 | 20 | Low |
| 15 | 24.1-39.9 | 48.5-55.9 | 0.39-0.65 | 22-23 | Low |

Example 16

Preparation of Linaclotide Formulation

The linaclotide formulation of Example 16 was produced essentially as described in Formulation Scheme B wherein Table 3 provides the amounts of cation, sterically hindered primary amine, binder, linaclotide and beads, while Table 4 provides the conditions under which the beads were coated:

TABLE 3

| Example | Cation Amount [ ] | Amine Amount [ ] | Binder Amount | Amount of Linaclotide | Beads Amount |
|---|---|---|---|---|---|
| 16 | CaCl$_2$•2H$_2$O 385.1 g [60] | Leucine 171.8 g [30] | Hypromellose 175.0 g | 73.5 g | Celphere CP-305 24.19 kg |

TABLE 4

| Example | Product Spraying Temp (° C.) | Inlet Temp (° C.) | Spray rate (g/min) | Atomization Pressure (bar) | Process Air Volume (cfm) | Product Drying Temp (° C.) |
|---|---|---|---|---|---|---|
| 16 | 64.9-65.1 | 80 | 150 | 2.0 | 515-564 | 54.9-55.0 |

Example 17

Preparation of Linaclotide Formulation

The linaclotide formulation of Example 17 was produced essentially as described in Formulation Scheme A except that the formulation contained 22.96 mg butylated hydroxyanisole (BHA), wherein Table 5 provides the amounts of cation, sterically hindered primary amine, binder, linaclotide and beads, while Table 6 provides the conditions under which the beads were coated.

TABLE 5

| Example | Cation Amount [ ] | Amine Amount [ ] | Binder Amount | Amount of Linaclotide | Beads Amount |
|---|---|---|---|---|---|
| 17 | CaCl$_2$•2H$_2$O 0.3745 g [20] | N/A | Hypromellose 0.6636 g | 0.2100 g | Celphere CP-305 33.99 g |

TABLE 6

| Example | Product Spraying Temp (° C.) | Inlet Temp (° C.) | Spray rate (mL/min) | Atomization Pressure (psig) | Air Flow |
|---|---|---|---|---|---|
| 17 | 33.5-34.8 | 47.7-48.6 | 0.56-0.74 | 26 | Low |

Example 18

Preparation of Capsules Containing Linaclotide Formulation

The linaclotide content on active beads may be measured as described in Example 21 or by other equivalent methods.

To form capsules suitable for oral administration, an appropriate amount of active beads is used to fill gelatin capsules (e.g., Size 2 gelatin capsules). An appropriate amount of active beads may contain 50 μg to 2 mg linaclotide per capsule with a range of ±5%. In some embodiments, the appropriate amount of linaclotide on active beads may be 50 μg, 67.5 μg, 100 μg, 133 μg, 150 μg, 200 μg, 266 μg, 300 μg, 400 μg, 500 μg, 600 μg, 700 μg, 800 μg, 900 μg, 1 mg, 2 mg, 4 mg or 6 mg. In a particular embodiment, the appropriate amount of linaclotide on active beads is 67.5 μg, 100 μg, 133 μg, 150 μg, 200

μg, 266 μg, 300 μg, 400 μg, 500 μg, 600 μg. In a more particular embodiment, the appropriate amount of linaclotide on active beads is 67.5 μg, 133 μg, 150 μg, 266 μg or 300 μg per capsule.

In another embodiment, an appropriate amount of active beads to fill a desired number of gelatin capsules is placed in a container. One or more pharmaceutically acceptable fillers or other pharmaceutically acceptable additives may be added, if desired, to the container. In some embodiments, a filler or additive is talc, leucine, microcrystalline cellulose or mannitol. The contents of the container are blended and the mixture is used to fill gelatin capsules with an appropriate amount of active beads containing linaclotide (e.g., 50 μg to 2 mg linaclotide per capsule with a range of ±5%).

In an alternative embodiment, an appropriate amount of active beads is used to fill gelatin capsules and one or more pharmaceutically acceptable fillers or other pharmaceutically acceptable additives are added to the gelatin capsules.

Example 19

Preparation of Capsules Containing Linaclotide Formulation

Preparation of the Coating Solution: First, 41.98 g of purified water was mixed with 1.13 g of hydrochloric acid in order to create a solution with a pH between 1.5 and 2.0. Next, 7.49 g of calcium chloride dihydrate and 6.68 g of leucine were added to the solution, which was then mixed for 30 minutes in order to produce a clear solution. The pH was tested, and 1.70 g of hydrochloric acid was added to produce a solution having a pH between 1.5 and 2.0. Next, 13.27 g of hypromellose (hydroxypropyl methylcellulose; Dow Chemical Company; Midland, Mich.) was added to the solution and the mixture was stirred for 60 minutes to achieve a clear solution. Next, 4.39 g of a linaclotide was added to the solution and mixed for 90 minutes. The pH of the solution was 1.73. This was the coating solution.

Preparation of the Active Beads: 674.5 g of microcrystalline cellulose beads (Celphere CP-305; Ashai Kasei Corporation (Tokyo; Japan) were added to a Wurster Column of a Glatt GPCG-2 Fluid Bed. The microcrystalline cellulose beads were fluidized and heated for 30 minutes at a product temperature of 60° C. Next, the coating solution was layered to the beads. The product temperature was controlled between 45° C. and 49° C. by an inlet temperature of 80° C., spray rate of 5.0-11 g/min, an atomization pressure of 2.0 bar, and air volume of 40 to 50 m$^3$h. After the entire coating solution was layered to the beads, the beads were dried for 10 minutes with a product temperature of 46.9° C. to 50.9° C. The product of this process was referred to as active beads.

Reverse phase liquid chromatography of linaclotide extracted from a formulation prepared as described above demonstrated that the extracted linaclotide and a linaclotide reference standard exhibited the same retention time and that there was no significant change in purity as a result of the formulation process.

To form capsules, 49.50 g of active beads were added to a clear bag. Next, 0.25 g of leucine, screened through a 60 mesh screen, was added to the bag. The bag was tied and mixed for 125 turns in order to blend all of the materials. Next, 0.25 g of talc, screened through a 60 mesh screen, was added to the bag. The bag was tied and mixed for 125 turns to blend all of the materials. Once all of the materials were blended, the mixture was used to fill Size 2 gelatin capsules at target weight of 227 mg/capsule with a range of ±5%.

Example 20

Preparation of Capsules Containing Linaclotide Formulation

Active beads were prepared according to Example 16. The active beads were tested for linaclotide content. Based on the assay of the active beads, an appropriate amount of active beads (96 mg-123 mg) were filled into size 2 hard gelatin capsules using an MG2 Futura encapsulation machine, to achieve a linaclotide concentration of 300 μg.

Active beads were prepared according to Example 15. The active beads were tested for linaclotide content. Based on the assay of the active beads, an appropriate amount of active beads (48 mg-62 mg) were filled into size 2 hard gelatin capsules using an MG2 Futura encapsulation machine, to achieve a linaclotide concentration of 150 μg.

Example 21

Measurement of Linaclotide Content and Purity

Linaclotide content and purity, as well as measurement of linaclotide-related substances may be determined by reverse phase gradient liquid chromatography using an Agilent Series 1100 LC System with Chemstation Rev A.09.03 software or equivalent. A YMC Pro™ C18 column (dimensions: 3.0×150 mm, 3.5 um, 120 Å; Waters Corp., Milford, Mass.) or equivalent is used and is maintained at 40° C. Mobile phase A (MPA) consists of water with 0.1% trifluoroacetic acid while mobile phase B (MPB) consists of 95% acetonitrile:5% water with 0.1% trifluoroacetic acid. Elution of linaclotide and its related substances is accomplished with a gradient from 0% to 47% MPB in 28 minutes followed by a ramp to 100% MPB in 4 minutes with a 5 minute hold at 100% MPB to wash the column. Re-equilibration of the column is performed by returning to 0% MPB in 1 minute followed by a 10 minute hold at 100% MPA. The flow rate is 0.6 mL/min and detection is accomplished by UV at 220 nm.

Samples for analysis are prepared by addition of the contents of linaclotide capsules to 0.1 N HCl to obtain a target concentration of 20 μg linaclotide/mL. 100 μL of this solution is injected onto the column.

Linaclotide content is measured by determining the linaclotide concentration in the prepared sample against a similarly prepared external linaclotide standard.

An example of an analysis of linaclotide by HPLC is shown in FIG. 1, wherein "Oxidation" refers to the linaclotide oxidation product, "Formaldehyde Imine" refers to the linaclotide formaldehyde imine product and "Hydrolysis" refers to the linaclotide hydrolysis product.

Example 22

Linaclotide Formulation Stability Testing

For the formulations of Examples 1-15 and 17, gelatin capsules were filled with approximately 225 mg of active beads. Five filled capsules were placed in plastic bottles. The bottles contained 1 to 2 g of desiccant and were induction sealed. The bottles were stored at 40° C./75% RH for six months.

Linaclotide content and purity as well as the amount of linaclotide-related substances were measured essentially as described in Example 21 or by an equivalent method. Results are provided in Table 7.

TABLE 7

| Example | Assay [w/w] % of Initial | Linaclotide (% of Initial) | Area % by HPLC Oxidation | Hydrolysis | Formaldehyde Imine |
|---|---|---|---|---|---|
| 1 | 107.56 | 96.88 (99.13) | 0.11 | 0.24 | 0.19 |
| 3 | 98.87 | 97.36 (99.42) | 0.07 | 0.52 | 0.15 |
| 4 | 95.67 | 95.61 (97.83) | 0.10 | 0.16 | 0.24 |
| 5 | 103.41 | 95.87 (98.68) | 0.07 | 0.25 | 0.24 |
| 6 | 99.46 | 93.64 (95.51) | 0.14 | 0.70 | 0.55 |
| 7 | 98.64 | 93.44 (95.36) | 0.45 | 1.45 | 0.63 |
| 8 | 92.81 | 88.20 (94.90) | 0.37 | 1.85 | 0.49 |
| 9 | 93.53 | 93.81 (96.55) | 0.2 | 0.41 | 1.06 |
| 10 | 77.12 | 84.85 (87.77) | 0.37 | 0.29 | 4.45 |
| 11 | 85.73 | 89.09 (91.63) | 1.18 | 0.49 | 1.38 |
| 12 | 33.60 | 41.98 (43.15) | ND | ND | ND |
| 13 | 87.69 | 91.91 (94.01) | 1.98 | 0.74 | 0.86 |
| 14 | 86.94 | 90.59 (92.70) | 0.25 | 0.54 | 1.23 |
| 15 | 87.71 | 87.54 (93.24) | 0.24 | 0.66 | 1.67 |
| 17 | 98.94 | 93.65 (95.16) | ND | 0.32 | 0.73 |

For the formulation of Example 16, gelatin capsules were filled with approximately 113 mg of total beads. 35 filled capsules were placed in plastic bottles. The bottles contained 2 g of desiccant and were induction sealed. The bottles were stored at 40° C./75% RH for one month.

Linaclotide content and purity as well as the amount of linaclotide-related substances may be measured essentially as described in Example 21 or by an equivalent method. Results are shown in Table 8.

TABLE 8

| Example | Assay [w/w] % of Initial | Linaclotide (% of Initial) | Area % by HPLC Oxidation | Hydrolysis | Formaldehyde Imine |
|---|---|---|---|---|---|
| 16 | 97.01 | 97.12 (99.79) | <0.1 | <0.1 | 0.34 |

Example 23

Isolation and Preparation of Linaclotide Hydrolysis Product

The linaclotide hydrolysis product occurs as a transformation of Asn in the 7 position to Asp (the numbering of linaclotide starts with 1 at the N-terminal Cys). Its structure is depicted below:

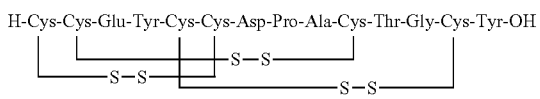

(SEQ ID NO: 2)

The linaclotide hydrolysis product has been independently synthesized for confirmation of identity using standard solid phase peptide synthesis techniques. The linaclotide hydrolysis product may also be prepared by other methods known in the art, e.g., by isolation from linaclotide preparations using chromatographic techniques or by recombinant expression of a nucleic acid encoding the linaclotide hydrolysis product (Cys Cys Glu Tyr Cys Cys Asp Pro Ala Cys Thr Gly Cys Tyr; SEQ ID NO:2), optionally followed by oxidation of the cysteine residues to form the disulfide linkages.

Example 24

Isolation and Preparation of Linaclotide Formaldehyde Imine Product

The formaldehyde imine product occurs as the addition of an imine to the N-terminal Cys (Cys1) via a formaldehyde-mediated reaction. A proposed structure of the product is depicted below:

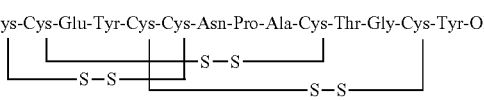

(SEQ ID NO: 3)

The linaclotide formaldehyde imine product has been independently synthesized for confirmation of identity by reacting linaclotide with formaldehyde (1:5 molar ratio) in absolute ethanol at room temperature for 4 days. The formaldehyde imine product may also be prepared by other methods known in the art, e.g., by isolation from linaclotide preparations using chromatographic techniques or by chemical peptide synthesis or recombinant expression of a nucleic acid encoding linaclotide followed by formylation as described herein or by other methods known in the art, optionally followed by oxidation of the cysteine residues to form the disulfide linkages.

Example 25

Isolation and Preparation of Linaclotide Oxidation Product

The linaclotide oxidation product has a molecular weight of 1542.8. The oxidation product most likely forms as the addition of a single oxygen atom to one of the six cysteinyl sulfurs in linaclotide. One potential structure of the product is depicted below, although one of skill in the art will recognize that the oxygen atom may be attached to any of the other five sulfurs:

(SEQ ID NO: 4)

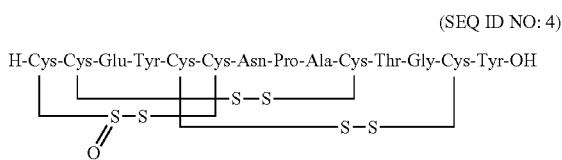

To support this identification, the linaclotide oxidation product has been produced by reacting linaclotide with hydrogen peroxide (3% aqueous) at room temperature or 40° C. for up to 24 hours. The resulting product is enriched in the oxidation product by 1-10%. The linaclotide oxidation product may also be prepared by other methods known in the art, e.g., by isolation from linaclotide preparations using chromatographic techniques or by chemical peptide synthesis or recombinant expression of a nucleic acid encoding linaclotide followed by oxidation of the cysteine residues to form the disulfide linkages followed by reacting linaclotide with hydrogen peroxide or similar oxidizing reagent to form the linaclotide oxidation product.

Example 26

Linaclotide Tablet Formation

Fluid Bed Granulation

Linaclotide, $CaCl_2$, leucine and polyvinyl pyrrolidone (PVP) K30 were dissolved in 0.0001N HCl to form the coating solution (see Table 9). Isomalt was charged to the bowl of the fluid bed. With fluidizing the isomalt powder, the drug solution was top-sprayed at a speed of ~10 g/min, with product temperature of ~40° C. to coat the powder with the coating solution. Upon finishing spraying, the linaclotide granules were dried for 30 minutes and the product was discharged.

TABLE 9

| Example | Cation Amount [ ] | Amine Amount [ ] | Binder Amount | Amount of Linaclotide | Filler Amount |
|---|---|---|---|---|---|
| 26A | $CaCl_2\cdot 2H_2O$ 15.4 g [60] | Leucine 6.9 g [30] | PVP K30 40 g | 3.08 g | Isomalt 935 g |

Dicalcium phosphate or Avicel were also used as filler for fluid bed granulation.

Wet Granulation

Linaclotide was weighed and dissolved under agitation in 250 g of 0.1 N HCl (pH 1.7) to form Solution 1 (see Table 10). $CaCl_2$ and leucine were weighed and dissolved under agitation in 100 g 0.1 N HCl to form Solution 2. Solution 1 and Solution 2 were mixed together under agitation to form the coating solution. Avicel was added to the bowl of a high shear granulator. With mixing at 500 rpm, the coating solution was added into the Avicel. Upon finishing adding the solution, the granules were mixed and chopped for 1 minute. The wet granules obtained were charged into the bowl of a fluid bed, and dried for 15 minute and then the linaclotide granules were discharged.

TABLE 10

| Example | Cation Amount [ ] | Amine Amount [ ] | Binder Amount | Amount of Linaclotide | Filler Amount |
|---|---|---|---|---|---|
| 26B | $CaCl_2\cdot 2H_2O$ 7.68 g [60] | Leucine 3.42 g [30] | N/A | 1.54 g | Isomalt 488 g |

In the wet granulation formula, the molar ratio of $CaCl_2$ and leucine to linaclotide was adjusted in the range of 60 to 100 and 30 to 50, respectively. Also, sucrose was added in one example. See Table 11.

TABLE 11

| Example | Strength (Linaclotide/Filler) | Filler | $CaCl_2$:Leu:Linaclotide | Sucrose | HCl |
|---|---|---|---|---|---|
| 26C | 600 µg/225 mg | Avicel | 60:30:1 | No | 0.1N |
| 26D | 600 µg/225 mg | Avicel | 80:40:1 | No | 0.1N |
| 26E | 600 µg/225 mg | Avicel | 100:50:1 | No | 0.1N |
| 26F | 600 µg/225 mg | Avicel | 60:30:1 | 5% | 0.1N |

Tablet Formulation

The linaclotide granules were blended with the following excipients (see Table 12) and compressed into tablets with a hardness of ~4 kp.

TABLE 12

| Ingredient Function | Weight in 200 mg tablet with 150 µg Linaclotide | Weight in 400 mg tablet with 300 µg Linaclotide | Weight in 800 mg tablet with 600 µg Linaclotide | Weight in 1600 mg tablet with 1200 µg Linaclotide |
|---|---|---|---|---|
| Linaclotide granules API | 53.4 mg | 106.8 mg | 213.6 mg | 427.2 mg |
| Isomalt Tablet filler | 134.1 mg | 268.2 mg | 536.4 mg | 1072.8 mg |
| Crospovidone Disintegrant | 10 mg | 20 mg | 40 mg | 80 mg |
| Magnesium stearate Lubricant | 1.5 mg | 3 mg | 6 mg | 12 mg |
| Talc Glidant | 1 mg | 2 mg | 4 mg | 8 mg |
| Total of dry material | 200 mg | 400 mg | 800 mg | 1600 mg |

Isomalt, starch 1500 or dicalcium phosphate were also used as the tablet filler based on the above formula (see Table 13).

TABLE 13

| Granulation | Filler | $CaCl_2$:leucine:Linaclotide | Tablet Filler |
|---|---|---|---|
| Fluid bed | isomalt | 60:30:1 | isomalt starch 1500 dicalcium phosphate |
| Fluid bed | Avicel | 60:30:1 | starch 1500 |
| Wet granulation | Avicel | 100:50:1 | starch 1500 |
| Wet granulation | Avicel | 60:30:1 + 5% sucrose | starch 1500 |

After two weeks storage at 40° C. and 75% relative humidity, all tablets described in Table 13 exhibited assay values of linaclotide is greater than 90%.

Examples 27-53

Preparation of Linaclotide Formulations

The linaclotide formulations of Examples 27-53 were produced essentially as described in Formulation Scheme A and Examples 1-15. The linaclotide coating solution contained 0.7% binder (w/v) and the coating solution was sprayed on Celphere CP-305 beads as described in Examples 1-15. Table 14 provides the type of cation, amine and/or other excipient along with their molar ratios relative to linaclotide, as well as the type of binder used, while Table 15 provides the conditions under which the beads were coated:

TABLE 14

| Example | Cation | Amine | Molar Ratio | Binder | Additive |
|---|---|---|---|---|---|
| 27 | $CaCl_2 \cdot 2H_2O$ | — | 20:0:1 | Hypromellose | — |
| 28 | $MnCl_2 \cdot 4H_2O$ | — | 20:0:1 | Hypromellose | — |
| 29 | KCl | — | 20:0:1 | Hypromellose | — |
| 30 | $AlCl_3 \cdot 6H_2O$ | — | 20:0:1 | Hypromellose | — |
| 31 | $CaCl_2 \cdot 2H_2O$ | Leucine | 60:30:1 | Hypromellose | — |
| 32 | Ca Alginate | Leucine | 60:30:1 | Hypromellose | — |
| 33 | $CaHPO_4$ | Leucine | 60:30:1 | Hypromellose | — |
| 34 | Ca Stearate | Leucine | 60:30:1 | Hypromellose | — |
| 35 | $CaSO_4 \cdot 2H_2O$ | Leucine | 60:30:1 | Hypromellose | — |
| 36 | $Zn(OAc)_2$ | Leucine | 60:30:1 | Hypromellose | — |
| 37 | $CaCl_2 \cdot 2H_2O$ | Isoleucine | 60:30:1 | Hypromellose | — |
| 38 | $CaCl_2 \cdot 2H_2O$ | Valine | 60:30:1 | Hypromellose | — |
| 39 | $CaCl_2 \cdot 2H_2O$ | Methionine | 60:30:1 | Hypromellose | — |
| 40 | $CaCl_2 \cdot 2H_2O$ | Phenylalanine | 60:30:1 | Hypromellose | — |
| 41 | — | Histidine | 0:20:1 | Hypromellose | — |
| 42 | — | Tryptophan | 0:20:1 | Hypromellose | — |
| 43 | $CaCl_2 \cdot 2H_2O$ | — | 0:20:1:20 (Vit. E) | Hypromellose | Vitamin E |
| 44 | — | 1-aminocyclohexane carboxylic acid | 0:20:1 | Hypromellose | — |
| 45 | — | cyclohexylamine | 0:20:1 | Hypromellose | — |
| 46 | — | 2-methylbutylamine | 0:20:1 | Hypromellose | — |
| 47 | — | chitosan | 0:20:1 | Hypromellose | — |
| 48 | $CaCl_2 \cdot 2H_2O$ | Leucine | 60:30:1 | Polyvinyl pyrrolidone | — |
| 49 | $CaCl_2 \cdot 2H_2O$ | Leucine | 60:30:1 | Methyl cellulose (Methocel A15) | — |
| 50 | $CaCl_2 \cdot 2H_2O$ | Leucine | 60:30:1 | Hydroxypropyl cellulose | — |
| 51 | NaCl | — | 20:0:1 | Hypromellose | — |
| 52 | $CaCl_2 \cdot 2H_2O$ | Leucine | 60:30:1 | Gelatin | — |
| 53 | $CaCl_2 \cdot 2H_2O$ | Glycine | 60:30:1 | Hypromellose | — |

* "Cation" refers to the cation contained in the salt used in the example, "Amine" refers to the sterically hindered primary amine, "Molar Ratio" refers to the molar ratio of the cation:amine:linaclotide:Additive (if applicable).

TABLE 15

| Example | Product Spraying Temp (° C.) | Inlet Temp (° C.) | Spray rate (g/min) | Atomization Pressure (psig) | Air Flow |
|---|---|---|---|---|---|
| 27 | 25.1-35.1 | 37.0-50.1 | 0.44-0.62 | 20 | Low |
| 28 | 24.1-35.8 | 37.3-50.9 | 0.30-0.61 | 18-20 | Low |
| 29 | 28.1-34.7 | 37.6-47.8 | 0.50-0.63 | 18 | Low |
| 30 | 29.8-35.0 | 33.9-50.2 | 0.32-0.47 | 20 | Low |
| 31 | 25.5-35.1 | 34.6-50.4 | 0.40-0.61 | 20 | Low |
| 33 | 30.4-35.2 | 38.7-51.0 | 0.48-0.52 | 20 | Low |
| 35 | 29.9-34.9 | 37.8-50.4 | 0.37-0.76 | 20 | Low |
| 36 | 29.9-35.4 | 38.0-50.1 | 0.38-0.50 | 21 | Low |
| 37 | 27.3-34.9 | 36.2-50.1 | 0.45-0.54 | 20 | Low |
| 38 | 27.6-36.2 | 36.9-47.3 | 0.43-0.66 | 20 | Low |
| 39 | 30.1-35.8 | 40.6-47.1 | 0.30-0.48 | 20 | Low |
| 40 | 31.7-37.5 | 41.3-51.0 | 0.40-0.67 | 18 | Low |
| 41 | 29.4-36.2 | 41.7-49.5 | 0.48-0.53 | 20 | Low |
| 42 | 31.0-38.6 | 42.4-51.2 | 0.52-0.64 | 20 | Low |
| 44 | 31.0-37.6 | 39.5-48.8 | 0.40-0.46 | 18 | Low |
| 45 | 28.7-36.5 | 37.1-49.2 | 0.49-0.61 | 18 | Low |
| 46 | 28.6-35.2 | 37.1-47.2 | 0.39-0.53 | 18 | Low |
| 47 | 33.4-38.7 | 40.6-48.5 | 0.48-0.47 | 18-26 | Low |
| 48 | 31.6-36.1 | 41.6-46.7 | 0.36-0.72 | 18 | Low |
| 49 | 28.5-36.5 | 36.8-48.1 | 0.45-0.51 | 18 | Low |
| 50 | 27.9-36.4 | 37.1-48.6 | 0.35-0.60 | 18 | Low |
| 51 | 29.3-37.9 | 36.7-49.2 | 0.42-0.55 | 18 | Low |
| 52 | 29.8-36.3 | 36.1-49.1 | 0.44-0.54 | 18 | Low |
| 53 | 28.9-35.8 | 36.5-47.7 | 0.45-0.52 | 18 | Low |

Processing issues were experienced during spraying on the beads for examples 32 (Calcium Alginate), 34 (Calcium Stearate) and 43 ($CaCl_2$:Vitamin E). Thus, the coating solution was mixed with the Celphere beads and the beads were dried on a tray.

Example 54

Linaclotide Formulation Stability Testing

For the formulations of Examples 27-53, gelatin capsules were filled with approximately 225 mg of active beads (600 μg linaclotide/capsule). Five filled capsules were placed in plastic bottles. The bottles contained 1 g of desiccant and were induction sealed. The bottles were stored at 40° C./75% RH for three months or six months.

Linaclotide content (μg/mg) and percent chromatographic purity (% CP) were measured essentially as described in Example 21 or by an equivalent method. Results are provided in Table 16A (three months stability) or Table 16B (six month stability).

TABLE 16A

| Example | Assay [w/w] % of Initial* | % CP | % CP [% of Initial] |
|---|---|---|---|
| 27 | 96.30 | 93.98% | 98.07 |
| 28 | 96.82 | 93.59% | 96.07 |
| 29 | 101.56 | 92.71% | 95.40 |
| 30 | 109.06 | 93.07% | 95.76 |
| 31 | 103.59 | 95.98% | 99.12 |
| 32 | 66.53 | 82.66% | 85.27 |
| 33 | 96.81 | 91.94% | 93.55 |
| 34 | 30.75 | 55.47% | 56.88 |
| 35 | 101.37 | 93.07% | 95.02 |
| 36 | 105.27 | 91.49% | 93.45 |
| 37 | 109.22 | 95.73% | 97.99 |
| 38 | 99.24 | 95.79% | 97.59 |
| 39 | 95.22 | 95.76% | 97.82 |
| 40 | 102.98 | 95.68% | 97.60 |
| 41 | 110.92 | 94.03% | 96.30 |
| 42 | 120.05 | 88.57% | 91.65 |
| 43 | 58.51 | 70.99% | 74.06 |
| 44 | 98.83 | 93.84% | 96.88 |
| 45 | 91.72 | 90.07% | 93.71 |
| 46 | 90.17 | 89.45% | 91.67 |
| 47 | 105.70 | 88.59% | 91.31 |
| 48 | 106.92 | 95.11% | 97.62 |
| 49 | 96.48 | 94.62% | 96.60 |
| 50 | 112.30 | 95.86% | 98.98 |
| 51 | 102.92 | 91.80% | 99.79 |
| 52 | 108.12 | 83.10% | 86.80 |
| 53 | 104.22 | 95.25% | 97.95 |

*Variability in the values for Assay [w/w % of Initial] reflects the imperfect control over content uniformity for these capsule lots, which manufactured at small scale.

It is believed that the difficulties encountered during processing and the resulting modified processing procedure for Examples 32, 34 and 43 (see above) could explain the lower stability observed in these samples.

TABLE 16B

| Example | Assay [w/w] % of Initial | Linaclotide (% of Initial) | Oxidation | Hydrolysis | Formaldehyde Imine |
|---|---|---|---|---|---|
| 27 | 91.58 | 89.68 (93.58) | 0.09 | 0.60 | 1.59 |
| 28 | 93.36 | 88.44 (90.78) | 0.24 | 0.41 | 1.55 |
| 29 | 93.73 | 87.79 (90.34) | 0.18 | 0.53 | 1.82 |
| 30 | 108.63 | 93.93 (96.65) | 0.39 | 1.11 | 0.44 |
| 31 | 94.53 | 86.83 (89.67) | — | 0.41 | 0.98 |
| 32 | 69.28 | 73.15 (75.46) | 0.97 | 1.93 | 1.69 |
| 33 | 88.91 | 85.96 (87.46) | 0.97 | 3.86 | 0.17 |
| 34 | 77.37 | 70.42 (72.21) | 0.67 | 0.99 | 1.78 |
| 35 | 95.34 | 88.85 (90.71) | 0.39 | 1.80 | 0.33 |
| 36 | 102.83 | 87.27 (89.14) | 3.31 | 1.86 | 0.21 |
| 37 | 99.33 | 87.23 (89.29) | — | 0.59 | 0.25 |
| 38 | 93.97 | 86.27 (87.89) | — | 0.42 | 0.45 |
| 39 | 87.78 | 85.23 (87.07) | — | 0.40 | 0.31 |
| 40 | 94.36 | 86.28 (88.01) | — | 0.46 | 0.41 |
| 41 | 104.28 | 90.04 (92.22) | 0.33 | 1.61 | 0.52 |
| 42 | 117.92 | 76.85 (79.52) | 0.14 | 1.21 | 0.10 |
| 43 | 54.21 | 59.54 (62.12) | 5.92 | 4.44 | 1.83 |
| 44 | 92.56 | 90.24 (93.17) | 0.16 | 1.47 | 0.54 |
| 45 | 76.23 | 79.57 (82.78) | 0.17 | 0.87 | 1.22 |
| 46 | 73.07 | 78.92 (80.88) | 0.51 | 0.66 | 0.65 |
| 47 | 97.65 | 82.73 (85.27) | 0.92 | 0.60 | 2.68 |
| 48 | 93.94 | 85.24 (87.49) | 0.05 | 0.69 | 0.20 |
| 49 | 51.65 | 63.46 (64.79) | 0.96 | 0.58 | 2.24 |
| 50 | 104.75 | 92.61 (95.62) | — | 0.38 | 0.48 |
| 51 | 94.15 | 88.19 (92.01) | — | 0.58 | 1.35 |
| 52 | 100.06 | 72.81 (75.62) | 0.06 | 0.49 | 0.41 |
| 53 | 95.74 | 89.80 (92.35) | 0.06 | 0.36 | 1.40 |

Chromatographic purity values for Examples 27-53 at the six-month time point appear atypically low, particularly with respect to the three-month time points for these samples. Relative trends for stabilizing or destabilizing effects can be established by comparison with Example 27 and Example 31 as internal reference experiments, for which the chromatographic purity values are approximately 6-8% lower than consistently observed in other studies that have been conducted (see, e.g., Examples 2 and 9). The three month data provided in Table 16A for the same formulations shows more typical chromatographic purity values. Thus, the low chromatographic purity values at six months are likely due to an insufficient desiccant capacity at six months for these particular storage conditions. This hypothesis is supported by the impurity peaks that are observed and that are indicative of exposure to moisture.

Example 55

Linaclotide Formulation Stability Testing at 25° C./60% RH for 24 Months

For the formulations of Examples 8-15 and 17, gelatin capsules were filled with approximately 225 mg of active beads. Five filled capsules were placed in plastic bottles. The bottles contained 1 g of desiccant and were induction sealed. The bottles were stored at 25° C./60% RH for 24 months.

Linaclotide content and purity as well as the amount of linaclotide-related substances were measured essentially as described in Example 21 or by an equivalent method. Results are provided in Table 17.

TABLE 17

| Example | Assay [w/w] % of Initial | Linaclotide (% of Initial) | Oxidation | Hydrolysis | Formaldehyde Imine |
|---|---|---|---|---|---|
| 8 | 94.36 | 94.58 (101.7) | 0.21 | 1.26 | 0.53 |

TABLE 17-continued

| Example | Assay [w/w] % of Initial | Linaclotide (% of Initial) | Area % by HPLC Oxidation | Hydrolysis | Formaldehyde Imine |
|---|---|---|---|---|---|
| 9 | 94.08 | 95.09 (97.86) | 0.14 | 0.36 | 0.93 |
| 10 | 80.80 | 87.82 (90.84) | 0.38 | 0.26 | 3.77 |
| 10a[1] | 89.29 | 91.55 (94.95) | 0.50 | 0.39 | 1.60 |
| 10b[2] | 88.41 | 91.19 (95.02) | 0.44 | 0.34 | 1.61 |
| 10c[3] | 72.35 | 72.36 (75.76) | 0.30 | 0.26 | 19.13 |
| 11 | 87.50 | 90.25 (92.82) | 1.03 | 0.42 | 1.94 |
| 12 | 62.82 | 66.77 (68.62) | 2.20 | 1.24 | 2.11 |
| 13 | 90.59 | 93.79 (95.93) | 1.21 | 0.65 | 0.77 |
| 14 | 91.41 | 94.88 (97.09) | 0.18 | 0.47 | 0.65 |
| 15 | 90.91 | 90.31 (96.18) | 0.17 | 0.56 | 1.64 |
| 17 | 91.45 | 92.92 (96.81) | 0.71 | 0.56 | 0.73 |

[1] As for Example 10 with additional protective coating of Aquacoat (Aquacoat Ethylcellulose Aqueous Dispersion, 15% w/w, FMC Biopolymer, ECD-30)
[2] As for Example 10 with additional protective coating of Opadry (Opadry AMB dispersion, 20% w/w, Colorcon).
[3] As for Example 10 with additional protective coating of Eudragit (Eudragit E PO, Degussa, Roehm Pharma Polymers; SLS, Stearic Acid)

Example 56

Linaclotide Tablet Formulation and Stability Testing

Active linaclotide granules were made by fluid bed granulation essentially as described in Example 26 using the reagents described in Table 18. The linaclotide granules were blended with the excipients described in Table 19 and compressed into tablets with a hardness of ~4 kp.

35 tablets were packaged in a 60 cc bottle with 5 gram desiccant and stored at 40° C./75% RH for up to 3 months or 30° C./65% RH for up to 3 months.

Linaclotide content and purity as well as the amount of linaclotide-related substances were measured essentially as described in Example 21 or by an equivalent method. Results are provided in Table 20.

TABLE 18

| Ingredients | Function | Granule, 150 μg linaclotide/53.7 mg granules |
|---|---|---|
| Linaclotide | API | 0.15 mg |
| Mannitol, USP | Granule filler | 50 mg |
| Leucine, USP | Stabilizer | 0.64 mg |
| CaCl$_2$•2H$_2$O, USP | Stabilizer | 0.72 mg |
| PVP K30, USP | Binder | 2.2 mg |
| HCl solution (pH 2.5) | — | — |

TABLE 19

| Ingredients | Function | Tablet (200 mg total weight) |
|---|---|---|
| Linaclotide granules | Active | 53.4 |
| Isomalt, USP | Tablet filler | 134.1 |
| Croscarmellose Sodium, USP | Disintegrant | 10 |
| Magnesium stearate, USP | Lubricant | 1.5 |
| Talc, USP | Glidant | 1.0 |

TABLE 20

| Condition | Time | Change in Assay % | Total Degradation |
|---|---|---|---|
| 40° C./75% RH | Initial | 100 | 2.27 |
| 40° C./75% RH | 1 month | 96.2 | 2.09 |
| 40° C./75% RH | 2 months | 102 | 2.15 |
| 40° C./75% RH | 3 months | 99.5 | 1.52 |
| 30° C./65% RH | 3 months | 100.1 | 1.19 |

Example 57

Linaclotide Capsule Formulation

The linaclotide formulation of Example 57 was produced essentially as described in Example 16. Table 21 provides the coating solution ingredients and their theoretical weights (mg/g) and (kg/Batch) for the complete Linaclotide Beads Drug Layer Solution. Table 22 provides the ingredients and theoretical weights (mg/g) and (kg/Batch) for the preparation for the Linaclotide Active Beads. The linaclotide formulation was encapsulated in hard gelatin capsules, size 2 (weight 61 mg), essentially as described in Example 20. The 150 μg linaclotide capsules contained 56 mg linaclotide beads (600 μg linaclotide/225 mg beads) while the 300 μg linaclotide capsules contained 113 mg linaclotide beads (600 μg linaclotide/225 mg beads).

TABLE 21

| Ingredients | Function | Theoretical Weight (mg/g) | Theoretical Weight (kg/batch) |
|---|---|---|---|
| Linaclotide | API | 2.67 | 0.067 |
| CaCl$_2$•2H$_2$O, USP, EP, BP, JP | Stabilizer | 15.41 | 0.385 |
| L-Leucine, USP | Stabilizer | 6.87 | 0.172 |
| Hydroxypropyl Methylcellulose, USP (Methocel E5 Premium LV) | Binder | 7.00 | 0.175 |
| Purified Water, USP | — | — | 16.666 |
| HCl (36.5-38.0), NF | — | — | 0.114 |

TABLE 22

| Ingredients | Function | Theoretical Weight (mg/g) | Theoretical Weight (kg/batch) |
|---|---|---|---|
| Linaclotide Beads Drug Layer Solution | Coating solution | 31.95 | 0.799 |
| Microcrystalline cellulose spheres NF (Celphere CP-305) | Beads | 968.05 | 24.201 |
| Final Total: Linaclotide Beads, 600 μg/225 mg) | Active beads | 1000 | 25.000 |

The invention claimed is:

1. A solid pharmaceutical composition for oral administration comprising a pharmaceutically acceptable carrier, linaclotide, a $Ca^{2+}$ cation and leucine, wherein linaclotide has the amino acid sequence Cys Cys Glu Tyr Cys Cys Asn Pro Ala Cys Thr Gly Cys Tyr (SEQ ID NO:1) and activates the guanylate cyclase C (GC-C) receptor.

2. The solid pharmaceutical composition of claim 1, wherein said $Ca^{2+}$ is provided as calcium chloride, calcium phosphate, or calcium sulfate.

3. The solid pharmaceutical composition of claim 1, further comprising one or more of a pharmaceutically acceptable binder or a pharmaceutically acceptable filler.

4. The solid pharmaceutical composition of claim 3, wherein the pharmaceutically acceptable binder is selected from polyvinyl alcohol, polyvinylpyrrolidone (povidone), a starch, maltodextrin or a cellulose ether.

5. The solid pharmaceutical composition of claim 3, wherein the pharmaceutically acceptable binder is a cellulose ether selected from methylcellulose, ethylcellulose, carboxymethylcellulose, hydroxyethyl cellulose, hydroxyethyl methylcellulose, hydroxypropyl cellulose and hydroxypropyl methylcellulose.

6. The solid pharmaceutical composition according to claim 3, wherein the pharmaceutically acceptable filler is cellulose, isomalt, mannitol or dibasic calcium phosphate.

7. The solid pharmaceutical composition of claim 6, wherein the cellulose is selected from microfine cellulose and microcrystalline cellulose.

8. The pharmaceutical composition according to claim 1, further comprising a hydrolysis product having a structure of

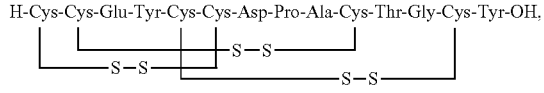

wherein the hydrolysis product comprises less than 2% by weight compared to the weight of the linaclotide.

9. The pharmaceutical composition of claim 8, wherein the hydrolysis product comprises less than 0.1% by weight or less than 0.05% by weight compared to the weight of the linaclotide.

10. The pharmaceutical composition according to claim 1, further comprising a linaclotide oxidation product having a molecular weight of 1542.8, wherein the linaclotide oxidation product comprises less than 2% by weight compared to the weight of the linaclotide.

11. The pharmaceutical composition according to claim 10, wherein the linaclotide oxidation product comprises less than 0.1% by weight or less than 0.05% by weight compared to the weight of the linaclotide.

12. The solid pharmaceutical composition according to claim 1, wherein the chromatographic purity of the linaclotide decreases by less than 10% after (a) 18 months of storage of the pharmaceutical composition at 25° C. at 60% relative humidity in a sealed container containing a desiccant or (b) 6 months of storage of the pharmaceutical composition at 40° C. at 75% relative humidity in a sealed container containing a desiccant.

13. The solid pharmaceutical composition according to claim 12, wherein the chromatographic purity of the linaclotide decreases by less than 9%, 8%, 7%, 6%, 5%, or 4% after (a) 18 months of storage of the pharmaceutical composition at 25° C. at 60% relative humidity in a sealed container containing a desiccant or (b) 6 months of storage of the pharmaceutical composition at 40° C. at 75% relative humidity in a sealed container containing a desiccant.

14. The solid pharmaceutical composition according to claim 1, wherein the chromatographic purity of the linaclotide decreases by less than 10% after (a) 24 months of storage of the pharmaceutical composition at 25° C. at 60% relative humidity in a sealed container containing a desiccant or (b) 6 months of storage of the pharmaceutical composition at 40° C. at 75% relative humidity in a sealed container containing a desiccant.

15. The solid pharmaceutical composition according to claim 1, wherein the chromatographic purity of the linaclotide is greater than or equal to 90% after (a) 18 months of storage of the pharmaceutical composition at 25° C. at 60% relative humidity in a sealed container containing a desiccant or (b) 6 months of storage of the pharmaceutical composition at 40° C. at 75% relative humidity in a sealed container containing a desiccant.

16. The solid pharmaceutical composition according to claim 1, wherein an assay value for linaclotide in a unit dosage form determined on a weight/weight basis decreases by less than 10%, after (a) 18 months of storage of the pharmaceutical composition at 25° C. at 60% relative humidity in a sealed container containing a desiccant or (b) 6 months of storage of the pharmaceutical composition at 40° C. at 75% relative humidity in a sealed container containing a desiccant.

17. The solid pharmaceutical composition according to claim 16, wherein the assay value for the linaclotide decreases by less than 9%, 8%, 7%, 6%, 5%, 4%, 3%, 2% or 1% after (a) 18 months of storage of the pharmaceutical composition at 25° C. at 60% relative humidity in a sealed container containing a desiccant or (b) 6 months of storage of the pharmaceutical composition at 40° C. at 75% relative humidity in a sealed container containing a desiccant.

18. The solid pharmaceutical composition according to claim 1, wherein an assay value of the linaclotide decreases by less than 10% after (a) 24 months of storage of the pharmaceutical composition at 25° C. at 60% relative humidity in a sealed container containing a desiccant or (b) 6 months of storage of the pharmaceutical composition at 40° C. at 75% relative humidity in a sealed container containing a desiccant.

19. The solid pharmaceutical composition according to claim 1, wherein an assay value for linaclotide determined on a weight/weight basis is greater than or equal to 90% after (a) 18 months of storage of the pharmaceutical composition at 25° C. at 60% relative humidity in a sealed container containing a desiccant or (b) 6 months of storage of the pharmaceutical composition at 40° C. at 75% relative humidity in a sealed container containing a desiccant.

20. The solid pharmaceutical composition of claim 2, wherein said $Ca^{2+}$ cation is provided as calcium chloride.

21. The solid pharmaceutical composition of claim 1, wherein the molar ratio of $Ca^{2+}$ cation:leucine:linaclotide is 40-100:20-50:1.

22. The solid pharmaceutical composition of claim 21, wherein the molar ratio of $Ca^{2+}$ cation:leucine:linaclotide is 100:30:1, 80:40:1, 80:30:1, 80:20:1, 60:30:1, 60:20:1, 50:30:1, 50:20:1, 40:20:1, 20:20:1, 10:10:1, 10:5:1, 5:10:1 or 5:5:1.

23. The solid pharmaceutical composition of claim 22, wherein the molar ratio of $Ca^{2+}$ cation:leucine:linaclotide is 60:30:1.

24. The solid pharmaceutical composition of claim 23, wherein the $Ca^{2+}$ cation is provided as calcium chloride.

25. The solid pharmaceutical composition of claim 22, wherein the solid pharmaceutical composition is a bead-containing capsule.

26. The solid pharmaceutical composition of claim 23, wherein the solid pharmaceutical composition is a bead-containing capsule.

* * * * *